(12) United States Patent
Markel et al.

(10) Patent No.: US 9,238,838 B2
(45) Date of Patent: Jan. 19, 2016

(54) MICRORNA PATTERNS FOR THE DIAGNOSIS, PROGNOSIS AND TREATMENT OF MELANOMA

(71) Applicants: TEL HASHOMER MEDICAL RESEARCH INFRASTRUCTURE AND SERVICES LTD., Tel Hashomer (IL); RAMOT AT TEL AVIV UNIVERSITY, Tel Aviv (IL)

(72) Inventors: Gal Markel, Tel Aviv (IL); Eyal Greenberg, Even Yehuda (IL); Jacob Schachter, Ramat Gan (IL)

(73) Assignees: Ramot at Tel Aviv University Ltd., Tel Aviv (IL); Tel Hashomer Medical Research Infrastructure and Services Ltd., Ramat Gan (IL)

( * ) Notice: Subject to any disclaimer, the term of this patent is extended or adjusted under 35 U.S.C. 154(b) by 0 days.

(21) Appl. No.: 14/265,337

(22) Filed: Apr. 29, 2014

(65) Prior Publication Data
US 2014/0235488 A1    Aug. 21, 2014

Related U.S. Application Data

(62) Division of application No. 13/813,805, filed as application No. PCT/IL2011/000622 on Aug. 1, 2011, now Pat. No. 8,980,549.

(60) Provisional application No. 61/369,711, filed on Aug. 1, 2010.

(51) Int. Cl.
| | |
|---|---|
| C12Q 1/68 | (2006.01) |
| C07H 21/02 | (2006.01) |
| C07H 21/04 | (2006.01) |
| A61K 48/00 | (2006.01) |
| A61K 31/7105 | (2006.01) |

(52) U.S. Cl.
CPC .......... *C12Q 1/6886* (2013.01); *A61K 31/7105* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC ................................................... C12N 15/113
See application file for complete search history.

(56) References Cited

U.S. PATENT DOCUMENTS

| | | |
|---|---|---|
| 7,635,563 B2 | 12/2009 | Horvitz |
| 7,897,356 B2 | 3/2011 | Klass |
| 2006/0105360 A1 | 5/2006 | Croce |
| 2007/0072204 A1 | 3/2007 | Hannon |
| 2008/0026951 A1 | 1/2008 | Brown |
| 2008/0076674 A1 | 3/2008 | Litman |
| 2008/0306006 A1 | 12/2008 | Croce |
| 2009/0031259 A1 | 1/2009 | Gray |
| 2009/0263803 A1 | 10/2009 | Beaudenon |
| 2010/0196426 A1 | 8/2010 | Skog |
| 2011/0107440 A1 | 5/2011 | Pivarcsi |

FOREIGN PATENT DOCUMENTS

| | | |
|---|---|---|
| WO | 2006/133022 | 12/2006 |
| WO | 2008/014008 | 1/2008 |
| WO | 2009/099905 A2 | 8/2009 |
| WO | 2009/120712 A2 | 10/2009 |

OTHER PUBLICATIONS

Chapman et al., (2011) Improved Survival with Vemurafenib in Melanoma with BRAF V600E Mutation. N. Engl J Med 364(26): 2507-2516.
Chiyomaru et al., (2010) miR-145 and miR-133a function as tumour suppressors and directly regulate FSCN1 expression in bladder cancer. Br J Cancer 102(5): 883-891.
Creighton et al., (2010) Molecular profiling uncovers a p53-associated role for microRNA-31 in inhibiting the proliferation of serous ovarian carcinomas and other cancers. Cancer Res 70(5): 1906-1915.
Felicetti et al., (2008) MicroRNA-221 and -222 pathway controls melanoma progression. Expert Rev Anticancer Ther 8 (11): 1759-1765.
Felicetti et al., (2008) The promyelocytic leukemia zinc finger-microRNA-221/-222 pathway controls melanoma progression through multiple oncogenic mechanisms. Cancer Res 68(8): 2745-2754.
Greenberg et al., (2011) Regulation of cancer aggressive features in melanoma cells by microRNAs. PLoS One 6(4): e18936.
Hughes et al., (2001) The cellular delivery of antisense oligonucleotides and ribozymes. Drug Discov Today 6(6): 303-315.
Kano et al., (2010) miR-145, miR-133a and miR-133b: Tumor-suppressive miRNAs target FSCN1 in esophageal squamous cell carcinoma. Int J Cancer 127(12): 2804-2814.
Lee et al., (2010) Network modeling identifies molecular functions targeted by miR-204 to suppress head and neck tumor metastasis. PLoS Comput Biol 6(4): e1000730.
Leidinger et al., (2010) High-throughput miRNA profiling of human melanoma blood samples. BMC Cancer 10: 262.
Liang et al., (2002) Optimizing the delivery systems of chimeric RNA.DNA oligonucleotides. Eur J Biochem 269(23): 5753-5758.
Liu et al., (2009) Uncovering growth-suppressive MicroRNAs in lung cancer. Clin Cancer Res 15(4): 1177-1183.
Markel et al., (2006) Inhibition of human tumor-infiltrating lymphocyte effector functions by the homophilic carcinoembryonic cell adhesion molecule 1 interactions. J Immunol 177: 6062-6071.
Mueller and Bosserhoff (2009) Role of miRNAs in the progression of malignant melanoma. Br J Cancer 101(4): 551-556.
Mueller et al., (2009) miRNA expression profiling in melanocytes and melanoma cell lines reveals miRNAs associated with formation and progression of malignant melanoma. J Invest Dermatol 129(7): 1740-1751.

(Continued)

*Primary Examiner* — Amy Bowman
(74) *Attorney, Agent, or Firm* — Rodney J. Fuller; Booth Udall Fuller, PLC

(57) ABSTRACT

The present invention relates to methods for diagnosing, staging, prognosticating and treating melanoma based on evaluating the expression of specific patterns of oncogenic or suppressive microRNA (miR) molecules in a patient in need thereof.

11 Claims, 16 Drawing Sheets

(56) References Cited

OTHER PUBLICATIONS

Nachmani et al., (2010) The human cytomegalovirus microRNA miR-UL112 acts synergistically with a cellular microRNA to escape immune elimination. Nat Immunol 11(9): 806-813.

Rosenfeld et al., (2008) MicroRNAs accurately identify cancer tissue origin. Nat Biotechnol 26: 462-469.

Segura et al., (2009) Aberrant miR-182 expression promotes melanoma metastasis by repressing FOXO3 and microphthalmia-associated transcription factor. Proc Natl Acad Sci U S A 106(6): 1814-1819; with Supporting Information.

Shapira-Frommer et al., (2011) Adoptive transfer of short-term cultured tumor-infiltrating lymphocytes (young TIL) in metastatic melanoma patients. J Clin Oncol 29: 2011 (suppl; abstr 8510).

Sonkoly et al., (2008) MicroRNAs and immunity: novel players in the regulation of normal immune function and inflammation. Semin Cancer Biol 18: 131-140.

Takahashi et al., (2009) MiR-107 and MiR-185 can induce cell cycle arrest in human non small cell lung cancer cell lines. PLoS One 4(8): e6677.

Wong et al., (2008) Mature miR-184 as Potential Oncogenic microRNA of Squamous Cell Carcinoma of Tongue. Clin Cancer Res 14(9): 2588-2592.

Levati et al., (2009) Altered expression of selected microRNAs in melanoma: antiproliferative and proapoptotic activity of miRNA-155. Int J Oncol 35(2): 393-400.

| -P (BENJAMINI YEKUTIELI) | & P(WESTFALL YOUNG) | -P (BENJAMINI HOCHBERG) | P VALUE | DIFFERENCE BETWEEN MEANS | KS GROUP 2 (PATIENTS) | KS GROUP 1 (CONTROL) | VS (CONTROL) (PATIENTS) |
|---|---|---|---|---|---|---|---|
| 0.755892892 | 0.50296 | 0.175046968 | 7.04E-05 | 1.587343965 | PASSED | PASSED | miR-29c |
| 0.99< | 0.86017 | 0.438192724 | 0.01103734 | 1.036439616 | FAILD | PASSED | miR-324-3p |
| 0.99< | 0.99< | 0.978580194 | 0.01439529 | 1.006096614 | PASSED | PASSED | miR-451 |
| 0.597567528 | 0.37837 | 0.138382547 | 0.01878212 | 1.749645783 | FAILD | PASSED | SNORD38B |
| 0.31217165 | 0.16047 | 0.072291592 | 0.03943152 | 1.181699903 | PASSED | PASSED | miR-374a |
| 0.99< | 0.99< | 0.978580194 | 0.04370590 | 0.864358646 | PASSED | PASSED | miR-150 |
| 0.0111199617 | 0.00343 | 0.002593567 | 0.05456865 | 0.975829391 | PASSED | PASSED | miR-29a |
| 0.0111199617 | 0.00829 | 0.002593567 | 0.13197250 | 0.813798973 | FAILD | PASSED | miR-312a |
| 0.38689494 | 0.23574 | 0.089595744 | 0.14581817 | 0.538498563 | PASSED | PASSED | miR-342-3p |
| 0.99< | 0.8071 | 0.386627616 | 0.39967106 | 0.492095522 | FAILD | PASSED | miR-339-3p |
| 1.0E-08 | 1.00E-08 | 1.00E-08 | 0.43828307 | 0.460792879 | PASSED | PASSED | miR-628-3p |
| 0.597567528 | 0.37902 | 0.138382547 | 0.76429132 | 0.222322788 | FAILD | PASSED | *miR-20a |
| 0.99< | 0.96155 | 0.680447401 | 0.88956680 | 0.066646935 | PASSED | PASSED | miR-503 |
| 0.99< | 0.99< | 0.978580194 | 0.89614082 | 0.042829677 | PASSED | PASSED | miR-197 |
| 0.755892892 | 0.50296 | 0.175046968 | 0.99< | 0.000630432 | PASSED | PASSED | miR-140-3p |

FIG.14

MICRORNA PATTERNS FOR THE DIAGNOSIS, PROGNOSIS AND TREATMENT OF MELANOMA

CROSS-REFERENCE TO RELATED APPLICATIONS

This application is a divisional of U.S. application Ser. No. 13/813,805, filed on Feb. 1, 2013 (now U.S. Publication No. 2013/0197060), which is the U.S. National Stage of International Application No. PCT/IL2011/000622, filed Aug. 1, 2011, which claims the benefit of U.S. Provisional Application No. 61/369,711, filed Aug. 1, 2010, the contents of each of which are herein expressly incorporated by reference for all purposes.

FIELD OF THE INVENTION

The present invention relates to methods for diagnosing, staging, prognosticating and treating melanoma based on evaluating the expression of specific patterns of oncogenic or suppressive microRNA (miR) molecules in a patient in need thereof.

BACKGROUND OF THE INVENTION

Melanoma accounts for 4% of all skin cancer diagnoses but contributes to 75% of deaths from skin cancer, where the incidence of melanoma and death rates from melanoma continue to rise, each year in the Western world.

In its early stages malignant melanoma can be cured by surgical resection, but once it has progressed to the metastatic stage it is extremely difficult to treat. Diagnosis of melanoma is commonly based on pathology and immunological staining and prognostication is mainly based on Breslow score (depth of invasion of the primary lesion).

MicroRNA (miR) molecules are major regulators of a large proportion of animal genes or the transcriptome. Association of various miRs with diseases or susceptibility to disease is known in the art. For example, U.S. Patent Application Publication No. 2007/0072204, discloses a method for diagnosing a subject with various cancers based on the expression level of mir17 (mir17-92 cistron).

Typical treatments of melanoma include surgery removal of the tumor, immunotherapy, chemotherapy and radiotherapy among others. The majority of all melanomas are caused by a missense mutation (V600E) in the B-Raf oncogene. Thus, various agents targeted to the inhibition of the V600E gene product have been developed and include, for example, the compound PLX4720 (known also as Vemurafenib), currently under human clinical studies. Additional novel approaches for melanoma therapy include agents which augment the anti-tumor immune response such as Ipilimumab, which blocks CTLA4 inhibition of lymphocyts, thereby enhancing the immune response directed to the tumor.

Creighton et al. (Cancer Res., Mar. 1, 2010; 70(5):1906-15) found miR-31 to be under-expressed in ovarian cancer cell lines, and showed that its forced expression induced p53-mediated apoptosis in different cell lines.

It has been shown by Liu et al. (Clin. Cancer Res., 15:1177-1183, 2009) and others that miR-133 is down-regulated in various cancer cell lines. Others have shown that miR133a is a tumor suppressor in bladder cancer (Chiyomaru et al., British Journal of Cancer 102(5):883-91, 2010) and in esophageal cell carcinoma (Kano et al., Int. J. Cancer, Mar. 2, 2010, Epub: http://www.ncbi.nlm.nih.gov/pubmed/20198616).

MiR-184 was also found to be associated with squamous cell carcinoma of tongue (Wong et al., Clin. Cancer Res., 14(9):2588-92, 2008).

Lee et al. (PLoS Comput. Biol., Apr. 1, 2010, 6(4): e1000730) indicates that miR-204 is an onco-suppressor in head and neck tumor metastasis.

U.S. Patent Application Publication No. 2006/0105360 discloses a method of diagnosing whether a subject has or is at risk of developing cancer, including melanoma, based on measuring the copy number of at least one miR gene, including, miR-301.

U.S. Patent Application Publication No. 2008/0026951, discloses the association of various miRs with different diseases, including the association of miR-17 with colon cancer; miR-31 with colon and thyroid cancers; miR-133a with cardiac hypertrophy and lupus; miR-184 with lupus and miR-204 with Alzheimer's disease.

U.S. Patent Application Publication No. 2008/0306006, discloses the association of various miRs, including, miR-31; miR-34a; miR-184prec; miR-185 and miR-204, with solid tumors, specifically, breast cancer; lung cancer, prostate cancer, stomach cancer, colon cancer and pancreatic cancer.

According to U.S. Patent Application Publication No. 2008/0076674 mi34a and miR185 are associated with breast cancer. Takahashi et al. (PLoS One, 4 (8):e6677, 2009) discloses that miR185 induces cell cycle arrest in lung cancer cell lines.

U.S. Patent Application Publication No. 2009/0263803 discloses that miR-29a and miR-29c, are differentially expressed in lymph nodes obtained from melanoma patients compared to healthy control subjects.

A method for diagnosing a cancer, including melanoma, in a subject, comprising determining an amount of one or more miRs including miR-324-3p, is disclosed in U.S. Patent Application Publication No. 2010/0196426, wherein if there is a measurable difference of said miR, the subject is diagnosed as having the cancer.

U.S. Pat. No. 7,897,356 discloses that miR-374, among other miRs, is a specific biomarker for melanoma. However, according to US 2011/0107440, the expression of miR-374, miR-29a, miR-29c, miR-324-3p and miR-451, among other miRs, is indicative of non-melanoma skin cancer.

Identification of miRNAs that regulate the aggressive phenotype of melanoma cells is disclosed by the inventors of the present invention in a paper entitled: "Regulation of cancer aggressive features in melanoma cells by microRNAs", published after the priority date of the present application (Greenberg et al. PLoS One. 2011 Apr. 25; 6 (4):e18936).

There is an unmet need for effective method of diagnosing, staging, prognosticating and treating metastatic melanoma.

SUMMARY OF THE INVENTION

The present invention relates to methods for the diagnosis, staging and prognostication of melanoma and metastatic melanoma, as well as, for treating metastatic melanoma, by evaluating the presence of patterns of oncogenic and suppressive miRNA patterns that specifically relate to the onset or prevention of metastatic melanoma.

The present invention further discloses methods for diagnosis and staging of melanoma by determining the presence of specific miRs expression patterns. It is now disclosed for the first time that specific miR expression patterns indicative whether or not a subject has or is susceptible to melanoma, are present in peripheral blood.

In addition, the present invention is based in part on the unexpected discovery that particular miR patterns, which includes miRs known to be generally associated with various diseases other than melanoma, where found to have specific roles in the suppression or oncogenesis of aggressive types of melanoma. As exemplified below, the suppressive miRs of the invention inhibited the proliferation, invasion ability and the ability to form tubes, in aggressive melanoma cells and tumors. It is further exemplified that the oncogenic miRs of the invention induced significant proliferation of poorly aggressive melanoma cells, with respect to control cells.

The present invention further discloses methods for predicting the responsiveness to melanoma therapy. In particular, as disclosed herein, miRs identified in the peripheral blood of a subject having melanoma or metastatic melanoma, may be used as predictors/biomarkers for the response of a subject to treatment with anti-cancer drugs, such as, Ipilimumab and Vemurafenib. Advantageously, the prediction of patient's responsiveness to melanoma therapy provides personalized medical tool, improves therapy management per patient, reduces exposure to side effects induced by unsuitable therapy and is cost effective among other advantages.

According to one aspect, the present invention provides a method for diagnosing melanoma in a subject, comprising:
  (a) obtaining from the subject a sample of peripheral blood comprising RNA; and
  (b) determining, in said RNA, the presence of a plurality of oncogenic miRNAs, comprising miRNAs selected from the group consisting of: miR-374a, miR-301a, SNORD-38b, miR-29c, miR-324-3p, miR-451 and miR-29a,
  wherein the presence of the plurality of oncogenic miRs is indicative of the subject having, or being susceptible to developing melanoma.

According to one embodiment, the plurality of oncogenic miRs further comprises one or more miRs selected from the group consisting of: miR-150, miR-342-3p, miR-197, miR-140-3p, miR-503, miR-339-3p, miR-628-3p and miR-20a*. Each possibility represents a separate embodiment of the invention.

According to another embodiment, the plurality of oncogenic miRs is selected from the group consisting of: miR-150, miR-451, miR-342-3p, SNORD38b, miR-324-3p, miR-29c, miR-197, miR-140-3p, miR-29a, miR-503, miR-339-3p, miR-628-3p, miR-20a*, miR-374a and miR-301a.

According to yet another embodiment, the plurality of oncogenic miRs is selected from the group consisting of: miR-374a, SNORD-38b and miR-301. Each possibility represents a separate embodiment of the invention.

According to yet another embodiment, the plurality of oncogenic miRs comprises SNORD-38b and one or more of miR-301 and miR-374. Each possibility represents a separate embodiment of the invention.

According to yet another embodiment, the plurality of oncogenic miRs is selected from the group consisting of: miR-374a, miR-29c, miR-324-3p, miR-451 and miR-29a.

According to yet another embodiment, the method comprises determining the presence of at least three oncogenic miRNA, or at least four oncogenic miRNAs, the presence of which is indicative of the subject having, or being susceptible to developing, melanoma. Each possibility represents a separate embodiment of the invention.

According to yet another embodiment, the method comprises determining the presence of miR-374a, and at least one miR selected from the group consisting of miR-301a, SNORD-38b, miR-29c, miR-324-3p, miR-451, miR-29a, miR-150, miR-342-3p, miR-197, miR-140-3p, miR-503, miR-339-3p and miR-20a. Each possibility represents a separate embodiment of the invention.

According to yet another embodiment, the plurality of oncogenic miRs are over-expressed at least 5 fold, at least 10 fold or at least 20 fold compared to expression of said plurality of miRs a healthy subject. Each possibility represents a separate embodiment of the invention.

According to yet another aspect the present invention provides a method for diagnosing metastatic melanoma, comprising:
  (a) obtaining a sample comprising RNA from a tumor of a subject; and
  (b) determining, in said RNA, the presence of a plurality of oncogenic miRs comprising miR-17 and at least one additional oncogenic miRNA selected from the group set forth in Table 1,
  wherein the presence of the plurality of said oncogenic miRs is indicative of the subject having, or being susceptible to developing, metastatic melanoma.

TABLE 1

Oncogenic human (hsa) miRNAs
Oncogenic miRs

| | | | |
|---|---|---|---|
| hsa-miR-603 | hsa-miR-15a* | hsa-miR-302b* | hsa-let-7f-2* |
| hsa-miR-299-5p | hsa-miR-19a* | hsa-miR-7 | hsa-miR-18a* |
| hsa-miR-886-5p | hsa-miR-183* | hsa-miR-26b* | hsa-miR-429 |
| hsa-miR-886-3p | hsa-miR-517b | hsa-miR-142-5p | hsa-miR-942 |
| hsa-miR-495 | hsa-miR-29b-1* | hsa-miR-190 | hsa-miR-572 |
| hsa-miR-137 | hsa-miR-30c-2* | hsa-miR-17* | hsa-miR-223 |
| hsa-miR-600 | hsa-miR-517a | hsa-miR-193a-3p | hsa-miR-892b |
| hsa-miR-558 | hsa-miR-373 | hsa-miR-801 | hsa-miR-92a-1* |
| hsa-miR-492 | hsa-miR-941 | hsa-miR-589 | hsa-miR-616 |
| hsa-miR-127-5p | hsa-miR-943 | hsa-miR-29a* | hsa-miR-182 |
| hsa-miR-125b-1* | hsa-miR-199b-5p | hsa-miR-200b | hsa-miR-99a* |
| hsa-miR-21* | hsa-miR-629 | hsa-miR-539 | hsa-miR-604 |
| hsa-miR-939 | hsa-miR-106a | hsa-miR-92a | hsa-miR-125b |
| hsa-miR-let-7e | hsa-miR-222 | hsa-miR-100 | hsa-miR-15b* |
| hsa-miR-661 | hsa-miR-138 | hsa-miR-18a | hsa-miR-139-5p |
| hsa-miR-210 | hsa-miR-30a* | hsa-miR-99a | hsa-miR-*222 |
| hsa-miR-15b | hsa-miR-let-7b | hsa-miR-708 | hsa-miR-935 |
| hsa-miR-19b | hsa-miR-18b | hsa-miR-27a* | hsa-miR-221 |
| hsa-miR-30e* | hsa-miR-27a | hsa-miR-*625 | hsa-miR-142-3p |
| hsa-miR-let-7a | hsa-miR-29a | hsa-miR-20a | hsa-miR-*424 |

*miR generated from the complementary strand.

According to one embodiment, the method comprises determining the presence of at least three oncogenic miRNA, or at least four oncogenic miRNAs, wherein at least one oncogenic miRNA is miR-17, such that the presence of which is indicative of the subject having, or being susceptible to developing, metastatic melanoma. Each possibility represents a separate embodiment of the invention.

According to yet another embodiment, the second sample obtained from a tumor comprises melanocytes.

According to yet another embodiment, the melanoma is selected from the group consisting of: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma and soft-tissue melanoma.

According to yet another aspect, the present invention provides a method for diagnosing melanoma in a subject, comprising
(a) obtaining from the subject a first sample of peripheral blood comprising RNA;
(b) determining, in said RNA, the presence of a plurality of miRNAs comprising miRNAs selected from the group consisting of miR-374a, miR-301a, SNORD-38b, miR-29c, miR-324-3p, miR-451 and miR-29a;
(c) identifying the subject as having, or being susceptible to, melanoma; and
(d) obtaining from a tumor of said subject a second sample comprising RNA and determining, in said RNA the presence of a plurality of oncogenic miRs comprising miR-17 and at least one additional miR selected from the group set forth in Table 1.
wherein the presence of the plurality of said oncogenic miRs is indicative of the subject having, or being susceptible to developing, metastatic melanoma.

According to one embodiment, the plurality of miRs further comprises miRs selected from the group consisting of: miR-150, miR-342-3p, miR-197, miR-140-3p, miR-503, miR-339-3p miR-628-3p and miR-20a*. Each possibility represents a separate embodiment of the invention.

According to another embodiment, the plurality of miRs is selected from the group consisting of: miR-374, SNORD-38b and miR-301. Each possibility represents a separate embodiment of the invention.

According to yet another embodiment, the plurality of miRs comprises SNORD-38b and one or more of miR-301 and miR-374. Each possibility represents a separate embodiment of the invention.

According to yet another embodiment, the plurality of miRs comprises miR-374, SNORD-38b and miR-301.

According to yet another embodiment, the plurality of miRs is selected from the group consisting of: miR-374a, miR-29c, miR-324-3p, miR-451 and miR-29a.

According to yet another embodiment, the plurality of miRs comprises miR-374a and at least one miR selected from the group consisting of: miR-301a, SNORD-38b, miR-29c, miR-324-3p, miR-451, miR-29a, miR-150, miR-342-3p, miR-197, miR-140-3p, miR-503, miR-339-3p, miR-628-3p and miR-20a*.

According to yet another aspect the present invention provides a method for diagnosing non-metastatic melanoma, comprising:
(a) obtaining a sample comprising RNA from a tumor of a subject; and
(b) determining, in said RNA, the presence of a plurality of suppressive miRs comprising miRNAs selected from the group consisting of: miR-31, miR-34a, miR-133a, miR-184, miR-185 and miR-204,
wherein the presence of the plurality of said suppressive miRs is indicative of the subject having, or being susceptible to developing, non-metastatic melanoma.

According to one embodiment, the plurality of suppressive miRs comprising miRNAs selected from the group set forth in Table 2:

TABLE 2

| Suppressive human (hsa) miRs Suppressive miRs | | | |
|---|---|---|---|
| hsa-miR-367 | hsa-miR-450b-5p | hsa-miR-363 | hsa-miR-616* |
| hsa-miR-211 | hsa-miR-500* | hsa-miR-7-2* | hsa-miR-148b* |
| hsa-miR-508-3p | hsa-miR-885-3p | hsa-miR-507 | hsa-miR-551b* |
| hsa-miR-509-5p | hsa-miR-340* | hsa-miR-525-5p | hsa-miR-587 |
| hsa-miR-509-3-5p | hsa-miR-887 | hsa-miR-876-3p | hsa-miR-579 |
| hsa-miR-506 | hsa-miR-501-3p | hsa-miR-551b | hsa-miR-675 |
| hsa-miR-184 | hsa-miR-649 | hsa-miR-133a | hsa-miR-455-5p |
| hsa-miR-485-5p | hsa-miR-487b | hsa-miR-381 | hsa-miR-545* |
| hsa-miR-31 | hsa-miR-412 | hsa-miR-146a* | hsa-miR-187 |
| hsa-miR-510 | hsa-miR-194 | hsa-miR-23b | hsa-miR-449b |
| hsa-miR-145 | hsa-miR-542-5p | hsa-miR-513-3p | hsa-miR-192 |
| hsa-miR-520d-5p | hsa-miR-641 | hsa-miR-190b | hsa-miR-362-3p |
| hsa-miR-508-5p | hsa-miR-513-5p | hsa-miR-652 | hsa-miR-483-5p |
| hsa-miR-382 | hsa-miR-216a | hsa-miR-582-3p | hsa-miR-672 |
| hsa-miR-139-3p | hsa-miR-520a-3p | hsa-miR-34a | hsa-miR-501-5p |
| hsa-miR-509-3p | hsa-miR-204 | hsa-miR-185 | hsa-miR-30d |
| hsa-miR-767-3p | hsa-miR-146a | hsa-miR-342-3p | hsa-miR-584 |
| hsa-miR-766 | | | |

*miR generated from the complementary strand

In some embodiments, determining the presence of the plurality of miRNAs according to the methods of the invention, comprises:
(a) reverse transcribing the RNA from the sample obtained from the subject to provide a set of target oligodeoxynucleotides;
(b) hybridizing the target oligodeoxynucleotides to a microarray comprising oncogenic miRNA-specific probe oligonucleotides to provide a hybridization profile for the test sample; and
(c) comparing the test sample hybridization profile to a hybridization profile generated from a control sample,
wherein oncogenic miRNA-specific probe oligonucleotides comprise any one or more of the following:
(i) miRNAs selected from the group consisting of: miR-31, miR-34a, miR-133a, miR-184, miR-185 and miR-204;

(ii) miRNAs selected from the group consisting of miR-374a, miR-301a, SNORD-38b, miR-29c, miR-324-3p, miR-451, miR-29a, miR-150, miR-342-3p, miR-197, miR-140-3p, miR-503, miR-339-3p, miR-628-3p and miR-20a*, (iii) miRNAs selected from the group set forth in Table 1; and (iv) miRNAs selected from the group set forth in Table 2.

and wherein an increase in the signal of a plurality of oncogenic miRNA relative to the control sample is indicative of the subject having, or being susceptible to developing, melanoma or aggressive melanoma. Each possibility represents a separate embodiment of the invention.

According to yet another embodiment, the method further comprises amplifying the target oligodeoxynucleotides prior to hybridization with the microarray.

According to yet another aspect, the present invention provides a pharmaceutical composition for treating metastatic melanoma, comprising a plurality of suppressive miRNAs or at least one miR-agonist capable of mimicking the activity of a plurality of suppressive miRNAs, and a pharmaceutically-acceptable carrier, the plurality of suppressive miRNAs comprises miRNAs selected from the group consisting of: miR-31, miR-34a, miR-133a, miR-184, miR-185 and miR-204. Each possibility represents a separate embodiment of the invention.

According to one embodiment, the plurality of suppressive miRNAs further comprises miRNAs selected from the group set forth in Table 2. Each possibility represents a separate embodiment of the invention.

According to another embodiment, the pharmaceutical composition comprises at least three suppressive miRNA and a pharmaceutically-acceptable carrier.

According to yet another embodiment, the pharmaceutical composition comprises at least one miR-agonist capable of mimicking the activity of the plurality of suppressive miRNAs.

According to yet another embodiment, the at least one miR-agonist is capable of mimicking the activity of at least three suppressive miRNAs.

According to yet another embodiment, the present invention provides a method of treating metastatic melanoma in a subject in need thereof, comprising administering to the subject an effective amount of a composition comprising a plurality of suppressive miRNA and a pharmaceutically-acceptable carrier, the plurality of suppressive miRNAs are selected from the group consisting of miR-31, miR-34a, miR-133a, miR-184, miR-185 and miR-204. Each possibility represents a separate embodiment of the invention.

According to yet another embodiment, the plurality of suppressive miRNAs are selected from the miRNAs set forth in Table 2.

According to yet another embodiment, the method comprises administering to the subject an effective amount of a composition comprising at least three suppressive miRNA. According to yet another embodiment, the method comprises administering to the subject an effective amount of a composition comprising at least four suppressive miRNA.

According to yet another embodiment, the melanoma is selected from the group consisting of: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma and soft-tissue melanoma. Each possibility represents a separate embodiment of the invention.

According to yet another embodiment, the method comprises administering to the subject an effective amount of a composition comprising at least one miR-agonist capable of mimicking the activity of at least three suppressive miRNAs.

According to yet another aspect, the present invention provides a pharmaceutical composition for treating metastatic melanoma, comprising at least one compound for inhibiting expression of a plurality of oncogenic miRNAs and a pharmaceutically-acceptable carrier, such that proliferation of aggressive melanoma cells is inhibited, wherein the plurality of oncogenic miRNA is selected from the group set forth in Table 1.

According to one embodiment, the at least one compound is selected from the group consisting of double-stranded RNA, small-interfering RNA, antisense nucleic acid, antagonist of the at least one miRNA and enzymatic RNA molecules. Each possibility represents a separate embodiment of the invention.

According to another embodiment, the compound is capable of inhibiting the expression of at least three oncogenic miRNAs.

According to yet another embodiment, at least one oncogenic miRNA is miR-17.

According to yet another embodiment, the present invention provides a method of treating metastatic melanoma in a subject in need thereof, comprising introducing into a cell or to a subject in need thereof an effective amount of the at least one compound for inhibiting expression of a plurality of oncogenic miRNAs.

According to yet another aspect the present invention provides a method of determining responsiveness of a patient diagnosed with melanoma to drug therapy, comprising;
(a) identifying a subject diagnosed with melanoma;
(b) obtaining a sample comprising RNA from the subject; and
(c) determining, in said RNA, the presence of a plurality of response associated miRs which are sensitive to said drug therapy,
wherein the presence of at least one miR is indicative of a positive outcome to the treatment.

According to one embodiment, drug therapy is selected from the group consisting of: Ipilimumab, Vemurafenib and a combination thereof. Each possibility represents a separate embodiment of the invention.

According to yet another embodiment, the melanoma is selected from the group consisting of: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma and soft-tissue melanoma. Each possibility represents a separate embodiment of the invention.

According to yet another embodiment the melanoma is metastatic melanoma.

According to yet another embodiment, the sample is obtained from a tumor or peripheral blood. Each possibility represents a separate embodiment of the invention.

According to yet another embodiment, responsiveness to Ipilimumab is measured by reduction in tumor size.

According to yet another embodiment the presence of at least one miR is determined by microarray analysis.

According to yet another embodiment drug therapy is combined with another melanoma therapy including but not limited to chemotherapy, radiation therapy and surgery. Each possibility represents a separate embodiment of the invention.

These and further objects, features and advantages of the present invention will become apparent from the following detailed description and appended claims.

BRIEF DESCRIPTION OF THE DRAWINGS

FIG. 14 presents analysis of 15 miRNAs.

DETAILED DESCRIPTION OF THE INVENTION

Figure 1:
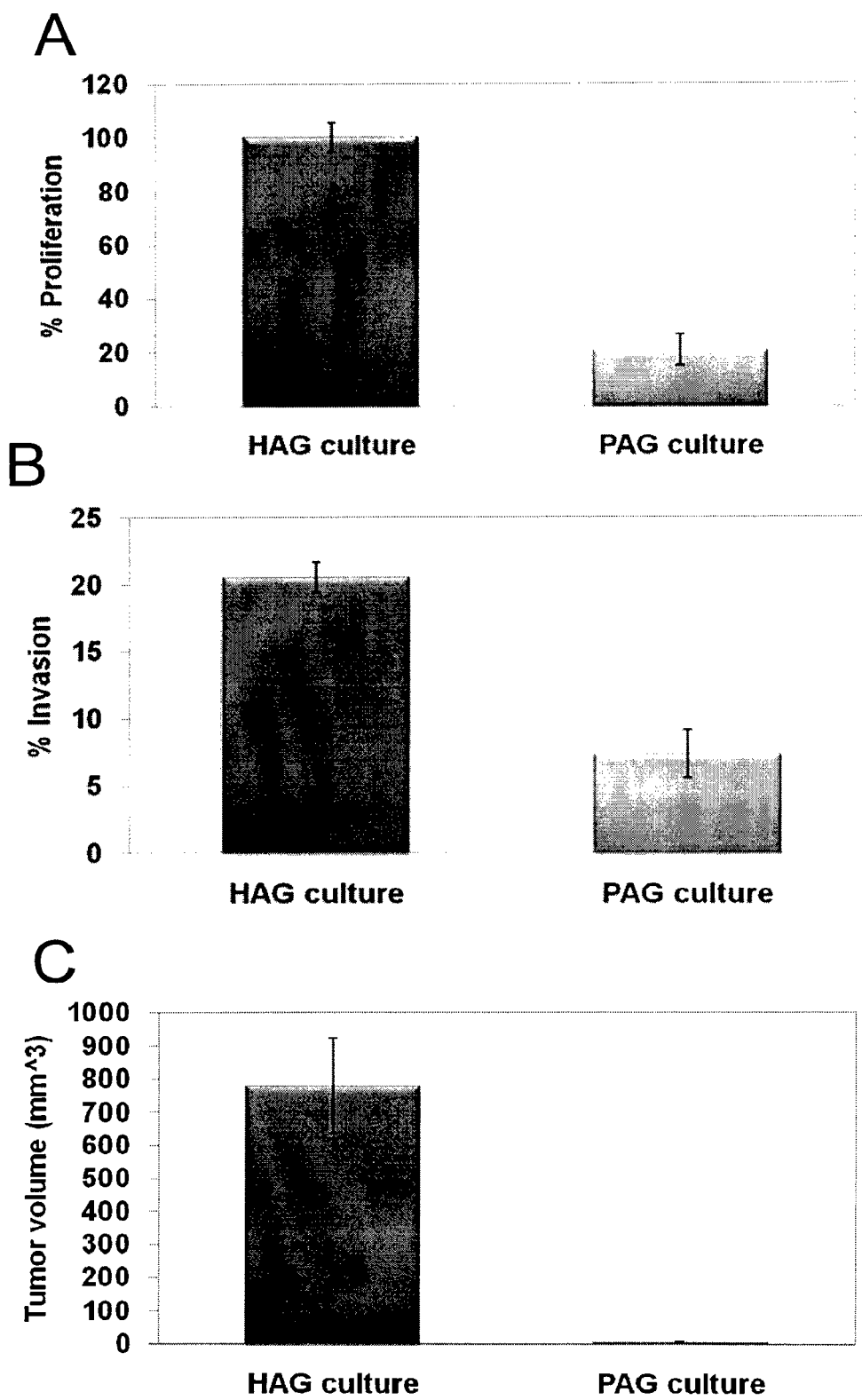
FIG. 1 presents the proliferation (A), invasion ability (B) and tumorigenic potential (C) of highly aggressive (HAG) and poorly aggressive (PAG) cells.

Melanoma is a malignant tumor of melanocytes (pigment producing cells) located predominantly in skin. Although only 4% of skin cancers are diagnosed with melanoma, melanoma account to 75% of death incidences from skin cancer. Unlike many other cancers, the incidence of melanoma increased by around 160,000 per year in the Western world.

The present invention relates to methods for the diagnosis, staging and prognosis of metastatic melanoma, as well as, methods and pharmaceutical compositions for treating metastatic melanoma.

Melanoma according to the present invention may refer to any of the following diseases: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma and soft-tissue melanoma.

The terms "malignant melanoma", "metastatic melanoma" or "aggressive melanoma" are interchangeable as used herein and include, but are not limited to, superficial spreading melanoma, nodular melanoma, lentigo maligna melanoma, acral melanoma, amelanotic melanoma and desmoplastic melanoma.

The terms "MicroRNA", "miR" or "miRNA" are used herein interchangeably for describing a class of non-coding RNA molecules of 18-24 nucleotides that exist in a variety of organisms, including mammals, and are conserved in evolution. miRNAs can be encoded in intergenic regions, hosted within introns of pre-mRNAs or within ncRNA genes. Many miRNAs also tend to be clustered and transcribed as polycistrons and often have similar spatial temporal expression patterns. MiRNAs have been found to have roles in a variety of biological processes including developmental timing, differentiation, apoptosis, cell proliferation, organ development, and metabolism and are major regulators of a large proportion of animal genes or the transcriptome. The present invention provides patterns of microRNA molecules that specifically relate to the presence or absence of melanoma, aggressive melanoma (oncogenic miRNAs) and indolent melanoma phenotype (suppressive miRNAs). Representatives of these miR patterns are shown herein to perform, in vitro and in vivo, as suppressors or inducers of aggressive melanoma.

Effective early diagnosis of melanoma, let alone, malignant melanoma is material since in its early stages this disease may be cured. The current approaches for diagnosis are primarily based on pathology and immunological staining while prognostication is mainly based on Breslow score (depth of invasion of the primary lesion). Molecular diagnosis is advantageous over the common methods as it can provide a reliable indication at the very early stages of onset, thereby enabling to manage and cure the disease. Further advantage of molecular diagnosis is that it enables continuous staging of the disease, which enables to target a therapy for each stage of the disease thereby providing an improved patient management.

The present invention provides patterns of oncogenic microRNA molecules that specifically relate to the presence melanoma. As shown below, the patterns of these microRNA of the invention strongly associate with melanoma. Accordingly, these miRNAs are particularly suitable for diagnosis of melanoma or for assessing susceptibility to developing melanoma.

According to the present invention, the patterns of oncogenic miRNAs which can be used to distinguish between healthy subjects and subjects having, or being susceptible to, melanoma, are circulating miRNA selected from the group consisting of: miR-150, miR-451, miR-342-3p, SNORD38b, miR-324-3p, miR-29c, miR-197, miR-140-3p, miR-29a, miR-503, miR-339-3p, miR-20a*, miR-628-3p, miR-374a and miR-301a.

The plurality of circulating miRs may be any cluster comprising SNORD-38b with any one or more of miR-374a, miR-301, miR-29c, miR324-3p, miR-451 and miR-29a. Each possibility represents a separate embodiment of the invention.

Alternatively, the plurality of circulating miRs may be any cluster comprising miR-374a and one or more of the following circulating miRs: miR-150, miR-451, miR-342-3p, SNORD38b, miR-324-3p, miR-29c, miR-197, miR-140-3p, miR-29a, miR-503, miR-339-3p, miR-628-3p miR-20a* and miR-301a.

In addition, the plurality of circulating miRs may be selected from miR-374a, miR-451, miR-324-3p, miR-29c, and miR-29a.

On the other hand, miRNA which can be used to distinguish between patients having metastatic melanoma and patients having non-metastatic melanoma, are non-circulating miRNA, derived from a tumor. These microRNAs include miR-17 among the other miRNAs listed in Table 1.

Preferably, for detection of aggressive melanoma (metastatic melanoma), it is required by the principles of the present invention to detect in a tumor a plurality of miRNAs selected from Table 1, wherein at least one miRNA is miR-17.

The method of the invention for determining the presence or absence of melanoma in a subject may further require identifying a cluster of at least three oncogenic miRNA, or at least four oncogenic miRNAs, from the aforementioned circulating miRNAs Over expression of miRs which distinguishes a healthy subject from a subject having melanoma may require that the plurality of oncogenic miRs are over expressed at least 5 fold, at least 10 fold or at least 20 fold difference when comparing the two.

Preferably, the sample comprising the RNA used for determining the presence or absence of melanoma (also termed "first sample"), based on circulating miRNAs is obtained from peripheral blood.

In addition, the present invention provides patterns of oncogenic microRNA molecules that specifically relate to aggressive melanoma. As exemplified hereinbelow, the patterns of oncogenic microRNA of the invention strongly associate with aggressive melanoma. Moreover, these oncogenic microRNA patterns are capable of inducing proliferation in poorly aggressive melanoma.

Determining whether melanoma is aggressive or not may be carried out after the person is diagnosed with melanoma according to the method of the invention, or before a person is diagnosed, provided that the staging (aggressive or not) is determined according to the presence of a plurality of miRs from Table 1.

In the step of staging melanoma, the RNA is derived from a sample, also termed "second sample" which is typically obtained from a tumor of the subject. The sample may contain melanocytes.

Accordingly, the oncogenic miRNAs of the invention listed in Table 1 are particularly suitable for diagnosis of aggressive melanoma or for assessing susceptibility to developing aggressive melanoma, as well as for molecular staging and prognostication of aggressive melanoma or for targeting therapeutic agents to aggressive melanoma. Assessment with the oncogenic miRNAs of the invention may be accompanied by other diagnostic techniques.

The terms "susceptibility to developing aggressive melanoma" or "being at a risk of developing melanoma and aggressive melanoma" refer to the probability of individuals to be diagnosed with aggressive melanoma. Thus, the methods of the invention include diagnostic tools for detecting aggressive melanoma as well as tools for predicting and/or assessing the susceptibility to develop this disease.

In one embodiment, the patterns of oncogenic miRNAs are selected from the group consisting of the miRNAs listed in Table 1 and combinations thereof. Specifically, the oncogenic miRNAs are selected from the group consisting of the following miRNAs and combinations thereof: hsa-miR-603, hsa-miR-15a*, hsa-miR-302b*, hsa-let-7f-2*, hsa-miR-299-5p, hsa-miR-19a*, hsa-miR-7, hsa-miR-18a*, hsa-miR-886-5p, hsa-miR-183*, hsa-miR-26b*, hsa-miR-429, hsa-miR-886-3p, hsa-miR-517b, hsa-miR-142-5p, hsa-miR-942, hsa-miR-495, hsa-miR-29b-1*, hsa-miR-190, hsa-miR-572, hsa-miR-137, hsa-miR-30c-2*, hsa-miR-17*, hsa-miR-223, hsa-miR-600, hsa-miR-517a, hsa-miR-193a-3p, hsa-miR-892b, hsa-miR-558, hsa-miR-373, hsa-miR-801, hsa-miR-92a-1*, hsa-miR-492, hsa-miR-941, hsa-miR-589, hsa-miR-616, hsa-miR-127-5p, hsa-miR-943, hsa-miR-29a*, hsa-miR-182, hsa-miR-125b-1*, hsa-miR-199b-5p, hsa-miR-200b, hsa-miR-99a*, hsa-miR-21*, hsa-miR-629, hsa-miR-539 and hsa-miR-604.

The invention also relates to methods for inhibiting or suppressing aggressive melanoma cells and tumors.

As used herein, "inhibiting or suppressing aggressive melanoma cells and tumors" refers to the inhibition or suppression of the proliferation of a metastatic melanoma cell, namely, killing the cell, or permanently or temporarily arresting or slowing the growth of the cell. This term also refers to inhibition of cell migration and invasion, thereby inhibition or suppression of the formation of metastases. Inhibition of cell proliferation can be inferred if the number of such cells in the subject remains constant or decreases after administration of the miR gene products or miR gene expression-inhibition compounds of the invention. An inhibition of cell proliferation can also be inferred if the absolute number of such cells increases, but the rate of tumor growth decreases.

Commonly, malignant melanoma is treated topically by surgical resection. However, this therapeutic approach is usually applicable only at early stages, and becomes less and less effective as the disease progresses to the metastatic stage. Atopical modalities include chemotherapy and immunotherapy, both of which offer 10-20% response with significant adverse effects. Therapy at the molecular level, as provided by the present invention, confers innumerable advantages, including, targeted therapy, tailored to the staging of the disease, thereby providing an improved patient management.

The method of the invention is based on suppression or inhibition of aggressive melanoma by introducing into a cell or a tumor or a subject, a pharmaceutical composition comprising at least one of the following as the pharmaceutical active ingredient: (a) a plurality, alternatively, at least three or more, suppressive microRNA molecules; (b) agonist(s) augmenting the activity of a plurality of suppressive microRNAs; or (c) antagonist(s) inhibiting the expression of a plurality of oncogenic miRNAs. The effective amount of the active ingredient in the pharmaceutical composition of the invention is determined during pre-clinical trials and clinical trials by methods familiar to physicians and clinicians. The pharmaceutical composition of the invention further comprises a suitable carrier. The pharmaceutical carrier may also comprise one or more of the following: a stabilizer, a surfactant, preferably a nonionic surfactant, and optionally a salt and/or a buffering agent.

According to one embodiment, the suppressive miRNAs in the pharmaceutical composition are selected from the group consisting of the miRNAs listed in Table 2 and combinations thereof. Specifically, the suppressive miRNAs are selected from the group consisting of the following miRNAs and combinations thereof: hsa-miR-367, hsa-miR-450b-5p, hsa-miR-363, hsa-miR-616*, hsa-miR-211, hsa-miR-500*, hsa-miR-7-2*, hsa-miR-148b*, hsa-miR-508-3p, hsa-miR-885-3p, hsa-miR-507, hsa-miR-551b*, hsa-miR-509-5p, hsa-miR-340*, hsa-miR-525-5p, hsa-miR-587, hsa-miR-509-3-

5p, hsa-miR-887, hsa-miR-876-3p, hsa-miR-579, hsa-miR-506, hsa-miR-501-3p, hsa-miR-551b, hsa-miR-675, hsa-miR-184, hsa-miR-649, hsa-miR-133a, hsa-miR-455-5p, hsa-miR-485-5p, hsa-miR-487b, hsa-miR-381, hsa-miR-545*, hsa-miR-31, hsa-miR-412, hsa-miR-146a*, hsa-miR-187, hsa-miR-510, hsa-miR-194, hsa-miR-23b, hsa-miR-449b, hsa-miR-145, hsa-miR-542-5p, hsa-miR-513-3p, hsa-miR-192, hsa-miR-520d-5p, hsa-miR-641, hsa-miR-190b, hsa-miR-362-3p, hsa-miR-508-5p, hsa-miR-513-5p, hsa-miR-652, hsa-miR-483-5p, hsa-miR-382, hsa-miR-216a, hsa-miR-582-3p and hsa-miR-672.

According to another embodiment, suppression or inhibition of aggressive melanoma is achieved by introducing into a cell or a tumor or a subject one or more agents that augment the activity of endogenous suppressive miRs, such as, an oligonucleotide agent or small molecule agent.

Embodiments of the invention provide specific compositions and methods that are useful in augmenting miRNA or pre-miRNA activity levels, in e.g., a mammal, such as a human. In particular, the present invention provides specific compositions and methods that are useful for enhancing activity levels of the suppressive miRNAs listed in Table 2, e.g., miR-31, miR-34a, miR-133a, miR-184, miR-185, miR-204 and combinations thereof.

A method of mimicking and preferably supplementing the effect of an miRNA or pre-miRNA in a cell of a subject, using compositions ('supermir') that are useful in augmenting miRNA or pre-miRNA activity levels, where the supermir is substantially single-stranded and includes a sequence that is substantially complementary to 12 to 23 contiguous nucleotides, and preferably 15 to 23 contiguous nucleotides, of a target sequence of an miRNA or pre-miRNA nucleotide sequence is provided in US Patent Application Publication No. 2009/031259.

The microRNA molecules of the invention can be introduced into a cell by any method known to those skilled in the art.

For example, the microRNA molecules can be injected directly into a cell, such as by microinjection. Alternatively, the molecules can be contacted with a cell, preferably aided by a delivery system.

Useful delivery systems include, for example, liposomes and charged lipids. Liposomes typically encapsulate oligonucleotide molecules within their aqueous center. Charged lipids generally form lipid-oligonucleotide molecule complexes as a result of opposing charges.

These liposomes-oligonucleotide molecule complexes or lipid-oligonucleotide molecule complexes are usually internalized in cells by endocytosis. The liposomes or charged lipids generally comprise helper lipids which disrupt the endosomal membrane and release the oligonucleotide molecules.

Other methods for introducing a microRNA molecule into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the microRNA oligonucleotide molecules over a prolonged period. The above methods are described in, for example, Hughes et al., Drug Discovery Today 6, 303-315 (2001); Liang et al. Eur. J. Biochem. 269 5753-5758 (2002); and Becker et al., In Antisense Technology in the Central Nervous System (Leslie, R. A., Hunter, A. J. & Robertson, H. A., eds), pp. 147-157, Oxford University Press.

The suppressive microRNA molecules can be also introduced into a mammal by any method known to those in the art. An example of a suitable mode of administration includes systemic administration, enteral or parenteral. Liquid or solid (e.g., tablets, gelatin capsules) formulations can be employed. The mode of administration may include targeting the microRNA molecule to a particular cell or tissue. Targeting of a microRNA molecule can be performed by any method known to those skilled in the art. For example, the microRNA molecule can be conjugated to an antibody or ligand specifically recognized by receptors on the cell.

Parenteral administration of the molecules include, for example intravenous, intramuscular, and subcutaneous injections. A molecule may be administered to a mammal by sustained release, as is known in the art. Sustained release administration is a method of drug delivery to achieve a certain level of the drug over a particular period of time.

Other routes of administration include intrabronchial or intranasal administration. Intrabronchial administration can include an inhaler spray. For intranasal administration, administration of a molecule of the present invention can be accomplished by a nebulizer or liquid mist.

As detailed above, the molecules of the present invention can be in a suitable pharmaceutical carrier. In this specification, a pharmaceutical carrier is considered to be synonymous with a vehicle or an excipient as is understood by practitioners in the art. Examples of carriers include starch, certain types of clay, gelatin, stearic acid or salts thereof, magnesium or calcium stearate, talc, vegetable fats or oils, gums and glycols.

The pharmaceutical carrier may also comprise one or more of the following: a stabilizer, a surfactant, preferably a nonionic surfactant, and optionally a salt and/or a buffering agent.

According to an alternative embodiment, the method comprises introducing into a cell or administering to the subject an effective amount of at least one compound for inhibiting expression of the plurality of oncogenic microRNA molecule of the invention such that proliferation of aggressive melanoma cells is inhibited. In a particular embodiment, the at least one miR expression-inhibition compound is specific for a plurality of miRs, or at least three miRs, selected from the group set forth in Table 1.

Suitable compounds for inhibiting miR gene expression include double-stranded RNA (such as short- or small-interfering RNA or "siRNA"), antisense nucleic acids, antagonist microRNAs, such as, antagomiRs, and enzymatic RNA molecules, such as ribozymes. Each of these compounds can be targeted to a given miR gene product and interfere with the expression of (e.g., inhibit translation of, induce cleavage or destruction of) the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a short or small interfering RNA or siRNA. siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

Antagomirs or "antagonist microRNA", as used herein, refer to engineered oligonucleotides (sometimes together with chemical modifications) that are used to antagonize miR functions, based on complementation and hybridization.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g. RNA, DNA, RNA-DNA chimeras, peptide nucleic acid (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Without wishing to be bound by any theory, it is believed that the antisense nucleic acids activate RNase H or another cellular nuclease that digests the miR gene product/antisense nucleic acid duplex.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

Any method for determining nucleic acid sequence and for analyzing the identified nucleotides for the presence of miRNA or an antisense thereof, known to a person skilled in the art, can be used according to the teachings of the present invention.

This includes the method for microRNA expression analysis disclosed in U.S. Pat. No. 7,635,563. The method includes use microarrays for detecting miRs, specifically, microRNA isolated from a sample is appended with linker(s) and a detectable labeling followed by contacting a microarray comprising at least 2 oligonucleotides with the detectably labeled microRNA and detecting binding of the detectably labeled microRNA to the microarray.

In some embodiments, determining, in the presence of the plurality of oncogenic miRNAs according to the methods of the invention, comprises:

(a) reverse transcribing the RNA from the sample obtained from the subject, to provide a set of target oligodeoxynucleotides;

(b) hybridizing the target oligodeoxynucleotides to a microarray comprising oncogenic miRNA-specific probe oligonucleotides, such as, miRNAs set forth in Table 1 or Table 2, to provide a hybridization profile for the test sample; and (c) comparing the test sample hybridization profile to a hybridization profile generated from a control sample, wherein an increase in the signal of a plurality of oncogenic miRNA relative to the control sample is indicative of the subject having, or being susceptible to developing, melanoma or aggressive melanoma. Each possibility represents a separate embodiment of the invention.

According to yet another embodiment, the method further comprises amplifying the target oligodeoxynucleotides prior to hybridization with the microarray.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1

Identification of miRs Patterns Associated with Aggressive Cancer Phenotype

The highly aggressive (HAG) C8161 and poorly aggressive (PAG) CS1-61 cutaneous melanoma cell lines were derived from different metastases from the same patient.

In order to identify miRNA patterns associated with aggressive phenotype of melanoma cells, a comparative qPCR-based high throughput analysis of human miRNAs (following ABI protocol) was performed on the melanoma sublines C8161-HAG and C8161-PAG.

Proliferation of HAG and PAG cells was measured with standardized XTT for 48 hours. The proliferation value for HAG cells was determined as 100%. Invasion ability of HAG and PAG cells was determined by 18 h matrigel invasion assay, which was corrected for proliferation. Tumorigenic potential of HAG and PAG cells was determined by SC injection of 1×106 cells into SCID-NOD mice. FIG. 1 shows the mean tumor volume within 18 days.

As shown in FIG. 1, the HAG cells are Highly Aggressive cells, manifested by high proliferation and invasion indices and by high tumorigenicity in immunodeficient mice. The PAG cells are Poorly Aggressive cells, which exert low proliferation and invasion indices and low tumorigenic potential in immunodeficient SCID mice.

Figure 2:
FIG. 2 shows the relative expression ratio of miRs in HAG cells vs. PAG cells (ratio=2-ΔΔCt).
Figure 3:
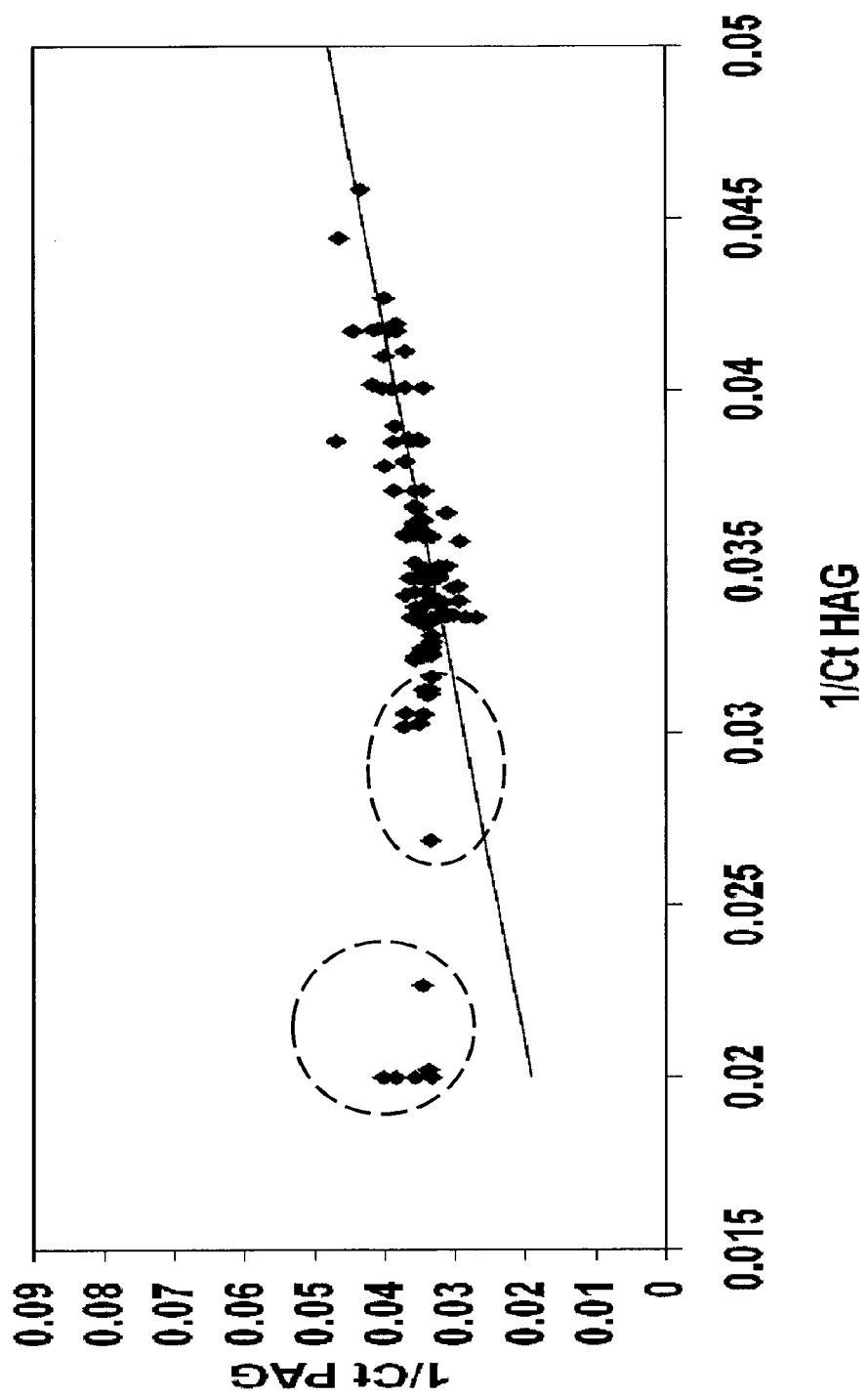
FIG. 3 exhibits differential miR expression among HAG and PAG cells, where randomly selected representative miRs falling off the diagonal line, which represent a significantly different expression level, are encircled.

The quantity of miRNAs in HAG and PAG cells was determined by qPCR (TaqMan) and normalized to the U6 endogenous control (FIG. 2). These miRNAs were expressed in both HAG and PAG cells within expression range (i.e. Ct<38; FIG. 3).

miRNAs that were not differentially expressed, or were expressed below detection levels in both sublines, were discarded. miRNAs that fall off the diagonal line represent a significantly different expression level (FIG. 3). This analysis yielded a list of oncogenic and suppressive human miRNAs, as follows:

a. miRs highly expressed in HAG and low in PAG cells. These miRs were classified as potentially "Oncogenic miRs". A list of oncogenic miRs is provided in Table 1.
  b. miRs of low expression in HAG and high in PAG cells. These miRs were classified as potentially "Suppressive miRs". A list of suppressive miRs is provided in Table 2.

Example 2

Forced Expression of Suppressive miRs Inhibit HAG Cells

Exemplar human miRs-31, -34a, -133a, -184, -185 and -204 were identified as suppressive miRs according to the HAG/PAG differential analysis. These miRs were cloned into PQCXIP retrovial vectors and introduced into HAG cells. An empty vector was used as control (Mock). Transfectants were tested in vitro in proliferation, invasion and tube formation in 3D matrix.

Proliferation of HAG transfectants was monitored by standardized XTT for 48 h and the values of Mock-transfected HAG cells were determined as 100%. Invasion ability of HAG transfectants was monitored by 18 h matrigel invasion assay with correction for proliferation where the values of Mock-transfected HAG cells were determined as 100%. Tube formation was monitored 48 h after seeding of transfectants in matrigel.

Figure 4:
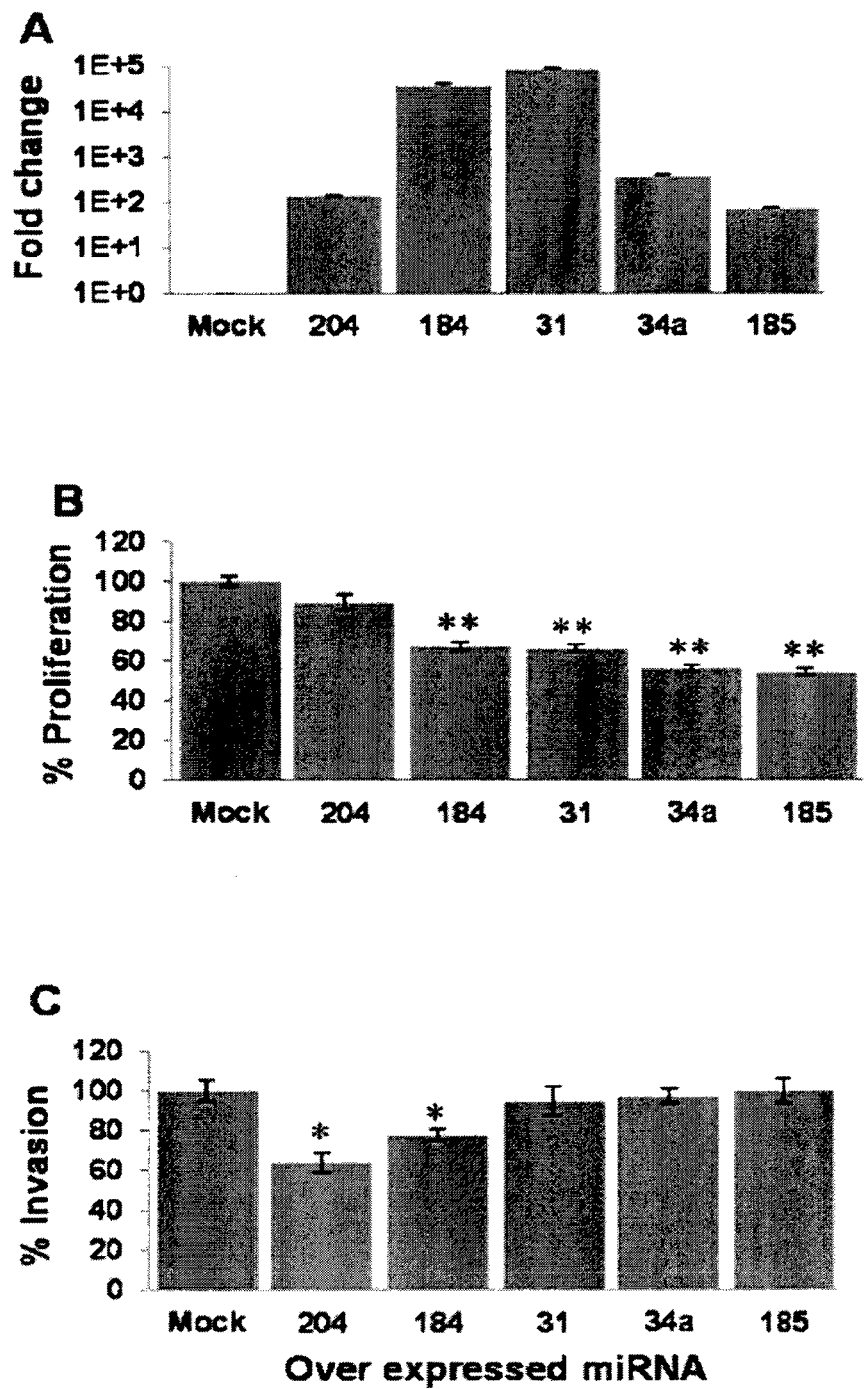
FIG. 4 presents inhibition of proliferation and invasion of melanoma cells by candidate suppressive miRNAs, through the fold change above Mock-transduced cells (A), net proliferation (B), invasion ability (C) and tube formation (D) of HAG transfectants expressing suppressive miRs.
Figure 4D:
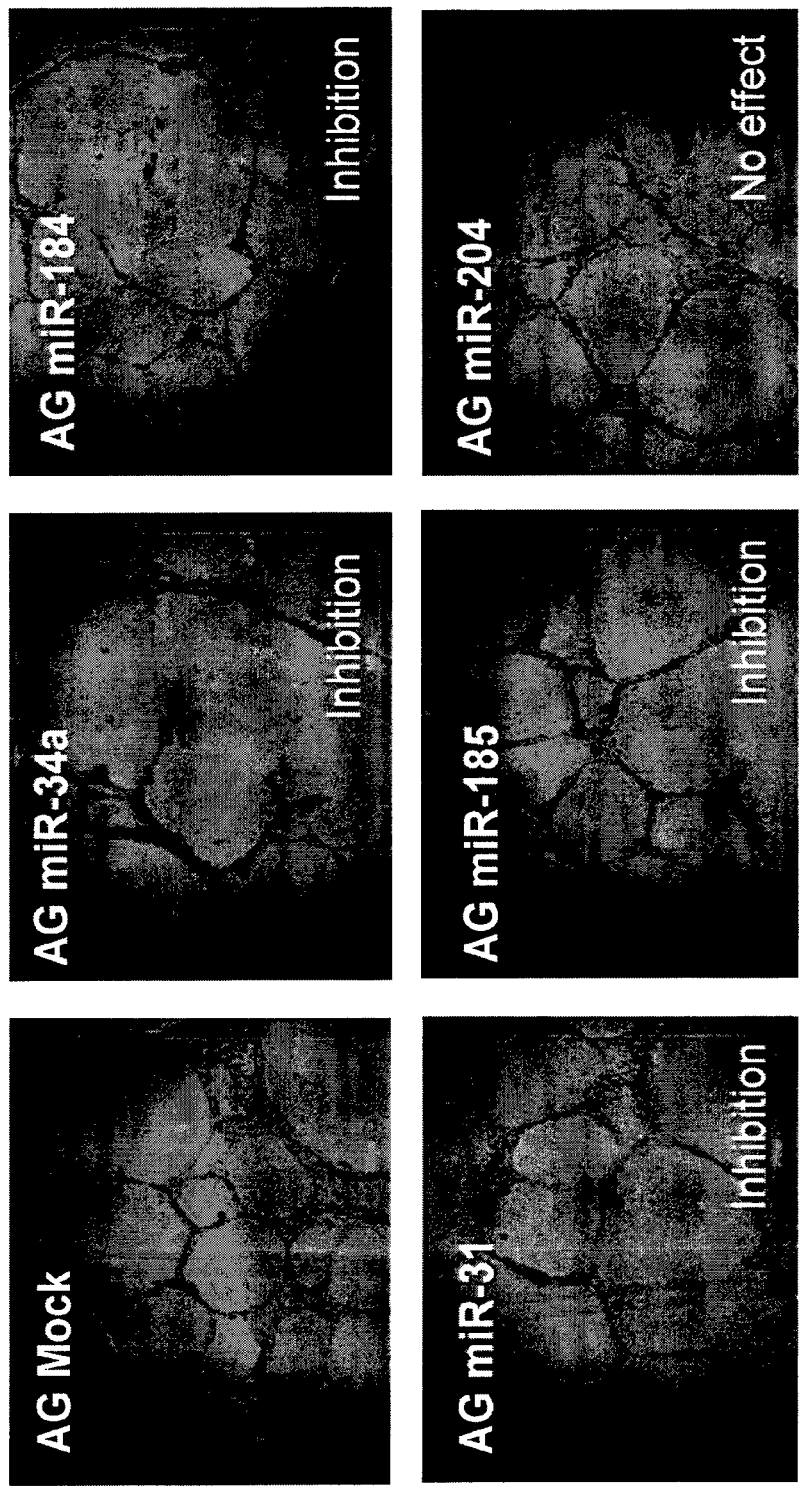

Forced expression of all of the above miRs in HAG cells resulted in inhibition of the abovementioned cancer functions (FIG. 4).

Specifically, an over-expression of at least 50-fold was conferred by real time PCT (FIG. 4A). The phenotype of the transduced cells was tested in vitro for proliferation, invasion and tube formation activities. Remarkably, a substantial and consistent inhibition in net proliferation was conferred by miR-31, miR-34a, miR-184 and miR-185 as compared to the control cell (FIG. 4B). miR-204 did not inhibit the proliferation of HAG cells (FIG. 4B). In contrast, miR-204 markedly inhibited the invasion activity of HAG cells (FIG. 4C). Invasion was similarly inhibited by miR-184, but not by the other suppressive miRNAs (FIG. 4C).

Figure 5:
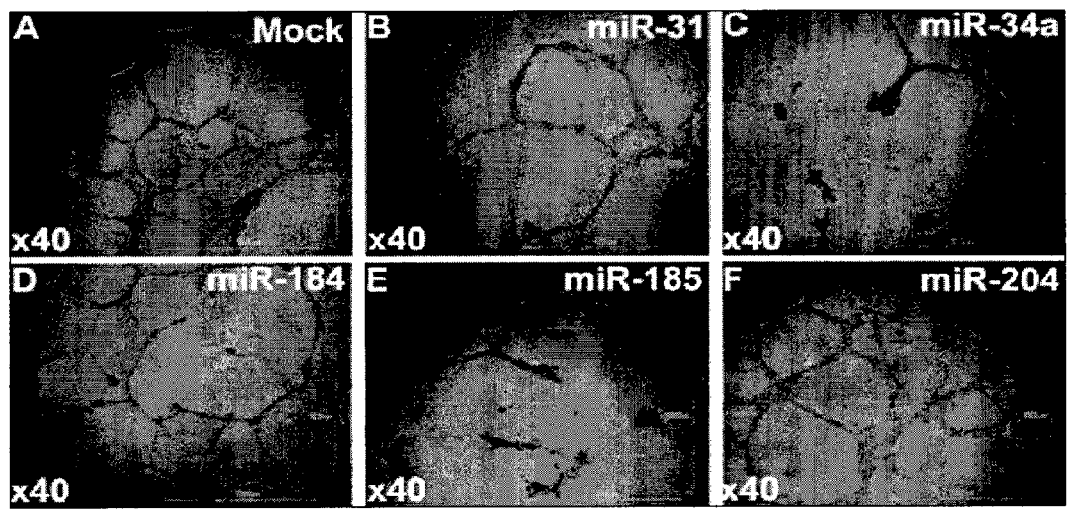
FIG. 5 demonstrates inhibition of tube formation by candidate suppressive miRNAs in culture of Mock-transduced HAG cells (A), miRNA-transduced HAG cell (B-F). Average tube formation was quantified using ImageJ analyze skeleton PlugIn (G; * denotes P<0.05, ** denotes P<0.01 (2-tailed t-test)).
Figure 5:
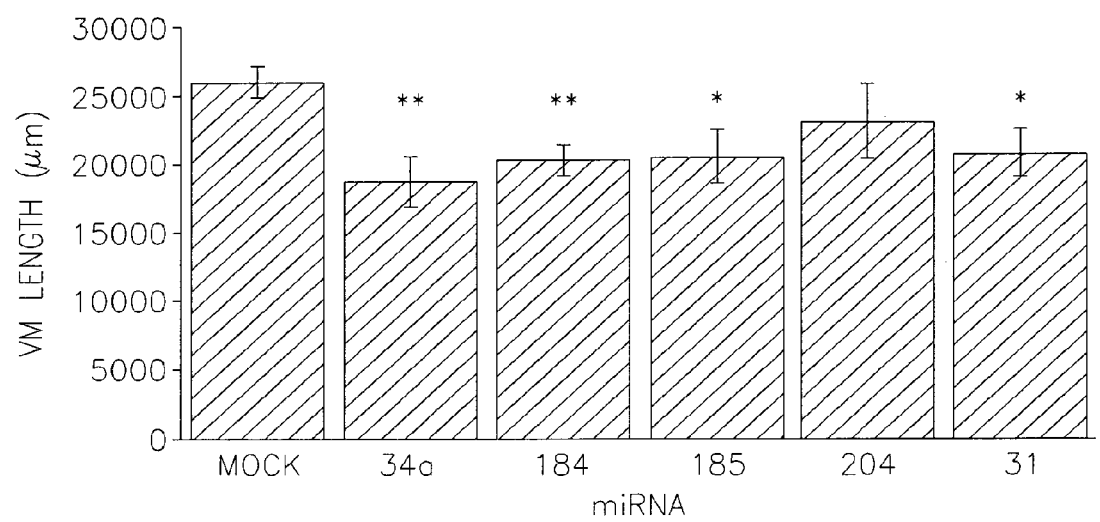

Tube formation activity was substantially inhibited by miR-34a and miR-185, and more mildly by miR-31 and miR-184, but not by miR-204, as compared to control (FIG. 5, A-F). Quantification of total tube length was performed using ImageJ (FIG. 5G).

Importantly, the qualitative assessment of micrographic captures (FIG. 5, A-F) concurred with the quantitative total length analysis (FIG. 5G). The differential effect of the miRNAs could not be simply attributed to their differential over-expression intensities (FIG. 4A). Almost all cells were viable when assayed, as evident by <5% positive trypan blue staining. Taken together, all live candidate suppressive miRNAs indeed exerted significant inhibitory effects on various aggressive features of melanoma cells. This concurs with their substantial down-regulation in the HAG cells (FIG. 2) and their overall low expression in clinical specimens (FIG. 3B). This also strengthens the high throughput miRNA screening used by the inventors and emphasizes its reliability.

Figure 6A:
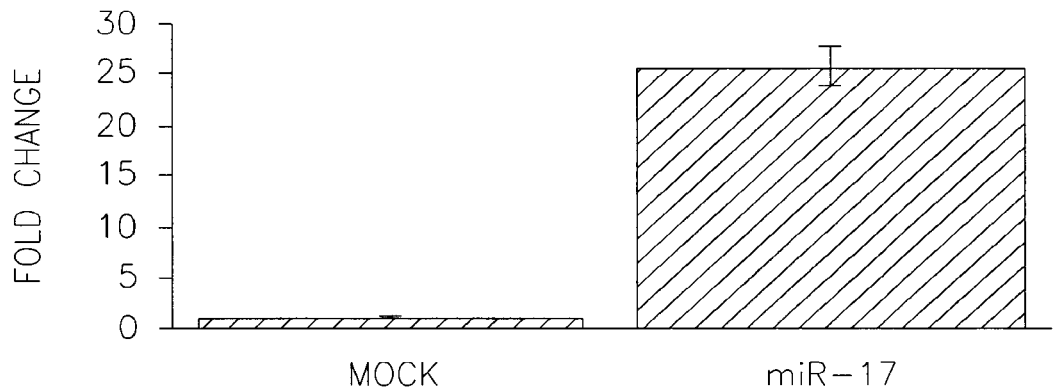
FIG. 6 shows enhanced proliferation of melanoma cells by candidate oncogenic miRNA: fold enhancement by miR-17 over-expression in PAG transductants, as compared to mock-transduced cells (A), net proliferation of the PAG transductants (B) and invasion activity of PAG transductants (C; ** denotes P<0.01 (2-tailed t-test)).
Figure 6B:
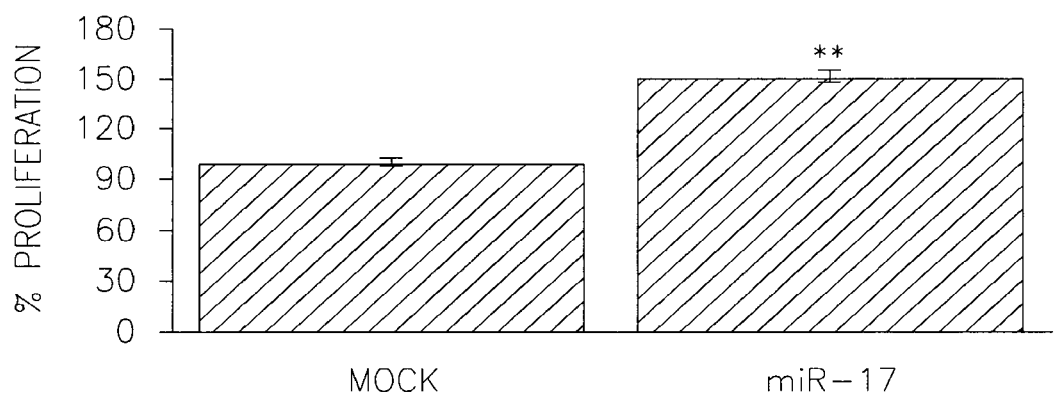
Figure 6C:
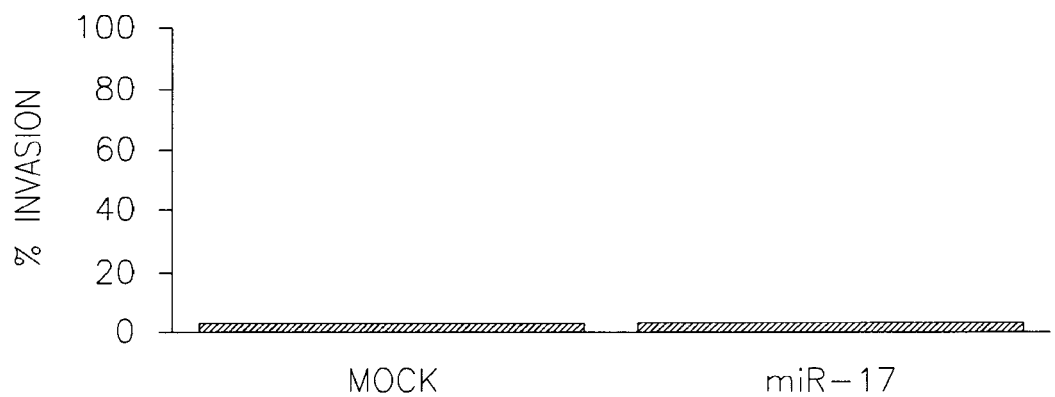

Since the miRNA 17-92 clusters' functional role in cancer is well established, yet never has it been tested in cutaneous melanoma, miR-17 was evaluated for its effect on the aggressiveness of PAG cells. miR-17 was cloned and stably over-expressed in the PAG cells. An empty vector served as control. A 25-fold over-expression of miR-17 was verified by real time PCR (FIG. 6A). Importantly, miR-17-transduced PAG cells displayed a significantly enhanced proliferative activity (FIG. 6B) but not invasive ability (FIG. 6C) or tube formation activity. These results support the potentially oncogenic effects of miR-17 in melanoma.

Example 3

Figure 7A:
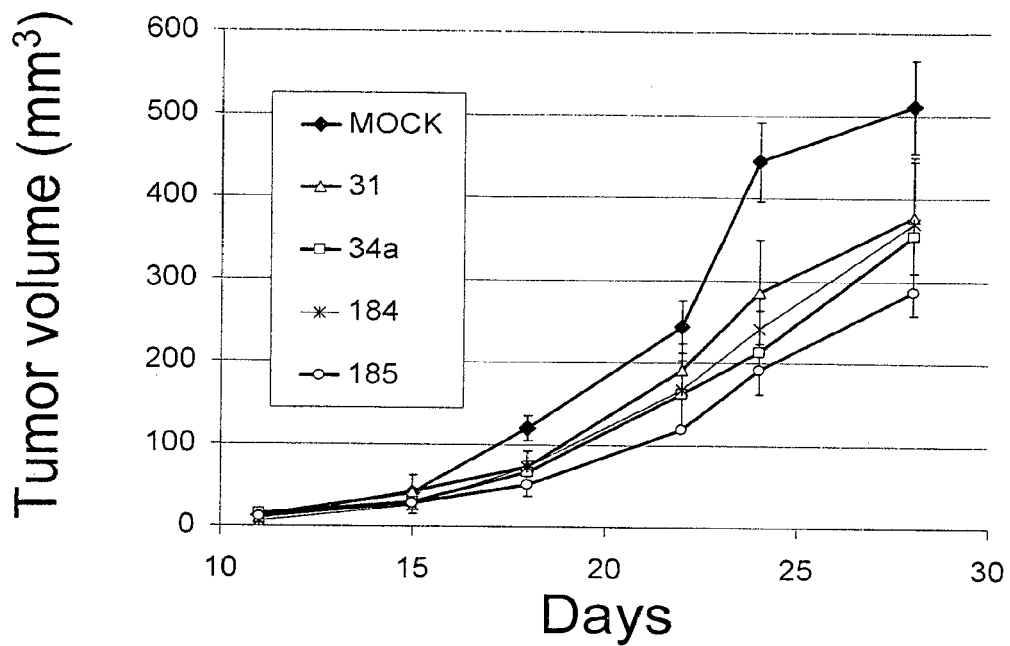
FIG. 7 exhibits growth inhibition of melanoma xenografts obtained by transfecting HAG transfectants expressing control (Mock; diamond) and suppressive miR-31 (triangle), miR-34a (square), iR-184 (asterisk) and miR-185 (circle) suppressive miRs in SCID-NOD mice, over time (A), the size of representative tumors at day 30 (B) and the percentage of mice bearing intra-abdominal macro-metastasis at day 30 (C).
Figure 7B:
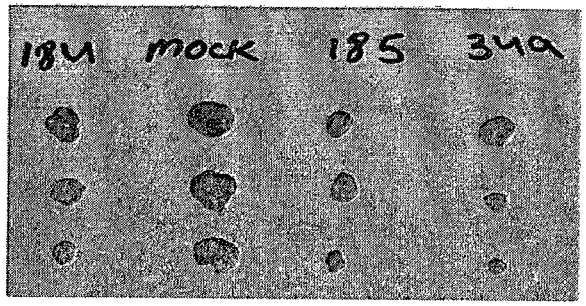

In Vivo Expression of Suppressive miRs miRs-31, -34a, -184 and -185 were also tested in vivo in order to confirm the results obtained in vivo. HAG transfectants (300,000 cells/mouse) were injected SC into SCID-NOD mice. Each type of transfectant was injected to 6-8 mice. Formation and growth of tumor masses were monitored 2-3 times a week using a caliper. On the day of the last measurements, mice were sacrificed and tumors were extracted. The results indicate that tumor growth is inhibited or slowed down upon transfection with miRs-31, -34a, -184 and -185 relative to mock (FIG. 7A). This observation was verified by the actual size of representative tumors extracted at day 30 of the treatment (FIG. 7B). In addition, the abdominal cavity of all mice was opened and inspected for the presence of macro-metastases. As shown FIG. 7C the percentage of mice bearing intra-abdominal macrometastases following transfection with -34a, -184 and -185 is significantly low relative to control. The numbers above each bar indicate the number of mice with metastases out of the total mice in the group (n=6-8).

Figure 7C:
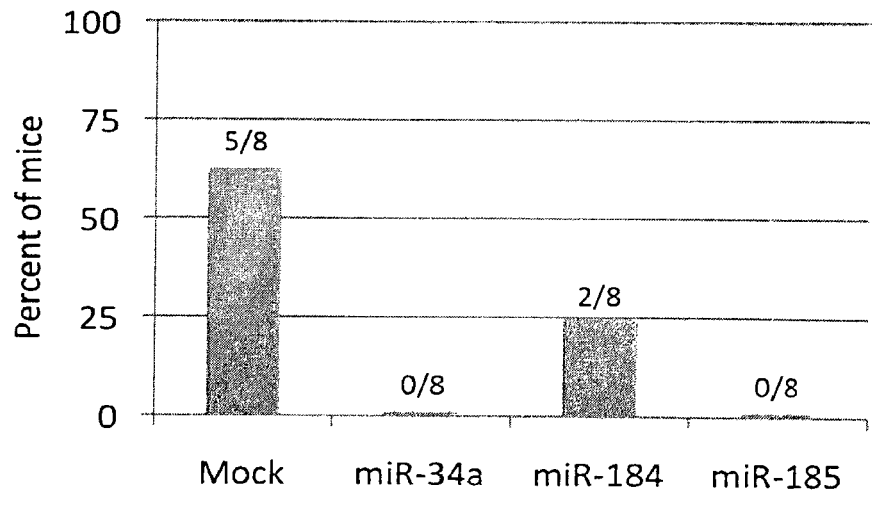

The results show that forced expression of all the miRNAs of the invention significantly inhibits HAG cell growth and spread in vivo (FIGS. 7A-C). These results further substantiate the role of the suppressive miRNAs of the invention.

Figure 8A:
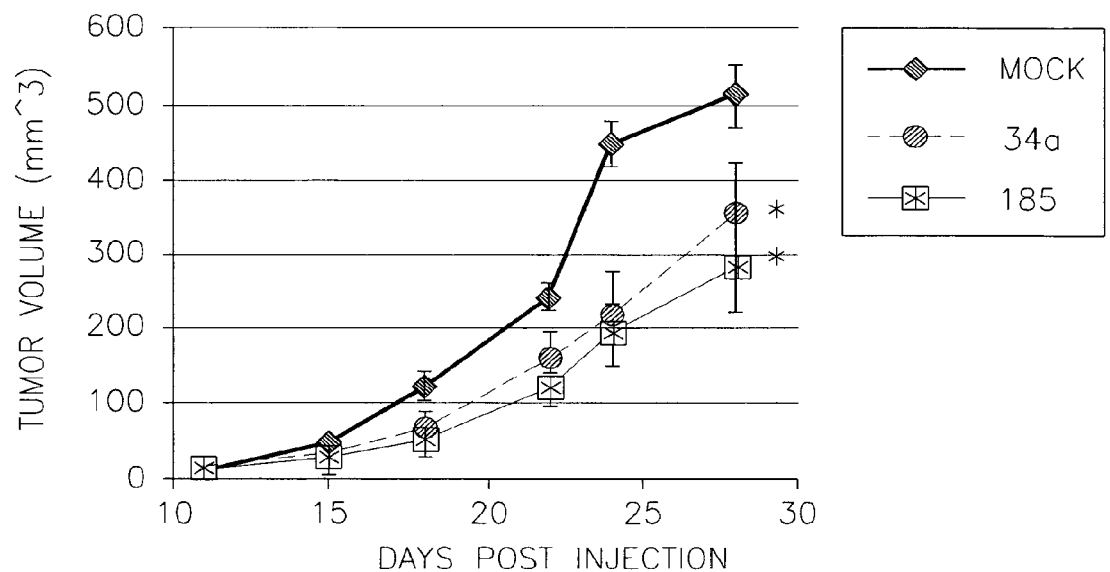
FIG. 8 shows tumor growth inhibition in vivo by control (Mock; diamond) and suppressive miR-34 (circle) and miR-185 (square) miRNAs: monitoring of tumor growth in SCID-NOD mice (A, n=7; Statistical significance was tested with 2-tailed-paired t-test); Mean weight of tumors explanted upon termination of the experiment (B; Statistical significance was tested with 2-tailed t-test); Over-expression of transduced miRNAs was confirmed upon termination of the experiment in all tumors with qPCR. (C; * denotes P<0.05).
Figure 8B:
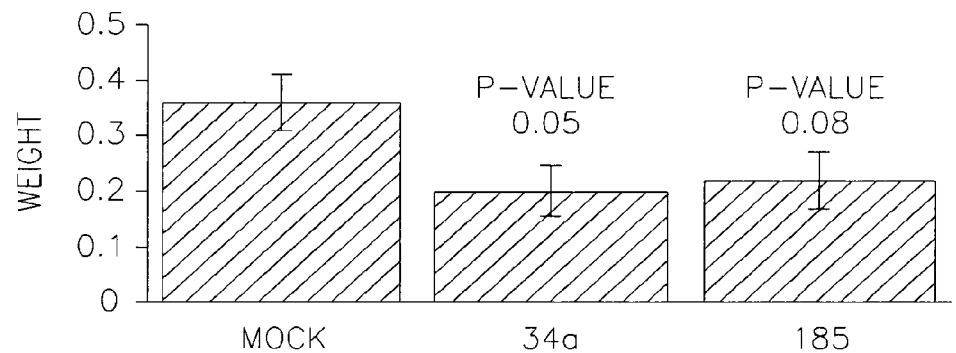
Figure 8C:
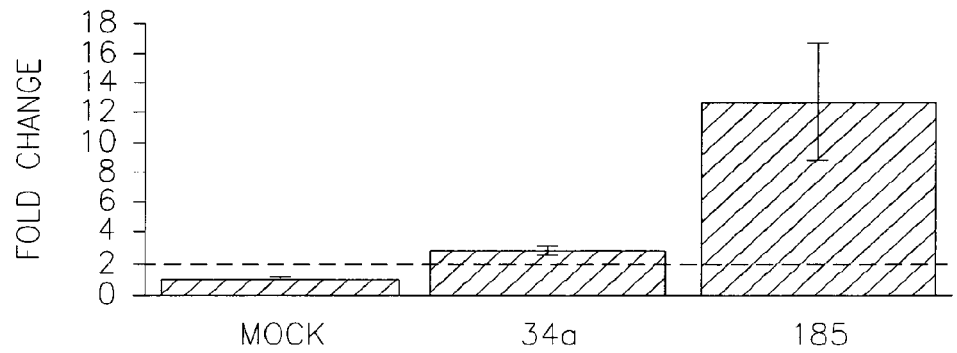

In another experiment, miRNAs were further assessed in vivo in melanoma xenograft models. The effect of the suppressive miRNAs, miR-34a and miR-185 on tumor growth was measured following subcutaneous injection of $3 \times 10^5$ HAG transductants. Tumor masses were monitored for 28 days post injection. Over-expression of specific miRNAs was confirmed pre-injection. Importantly, a statistically significant inhibition in tumor growth was observed in both miR-34a and miR-185 transductants, as compared to control tumors (FIG. 8A). Concurring with these results, ex-vivo weighing of tumor explants upon termination of the experiments confirmed that the average tumor mass of both miR-34a and miR-185 transductants was lower than Mock transduced tumors (FIG. 8B). The in vivo over-expression of the transduced miRNAs was confirmed in the tumor explants (FIG. 8C). These results corroborate with the expression results and functional suppressive effects demonstrated in vivo (FIGS. 4-5).

Example 4

Forced Expression of Oncogenic miRs Facilitate Cancer Features of PAG Cells

Exemplar human miR-17 was identified as an oncogenic miR according to the HAG/PAG differential analysis. This miR was cloned into PQCXIP retrovial vectors and introduced into PAG cells. An empty vector was used as control (Mock). Transfectants were tested in vitro for proliferation by standardized XTT assay, invasion and tube formation in a 3D matrix.

Figure 9:
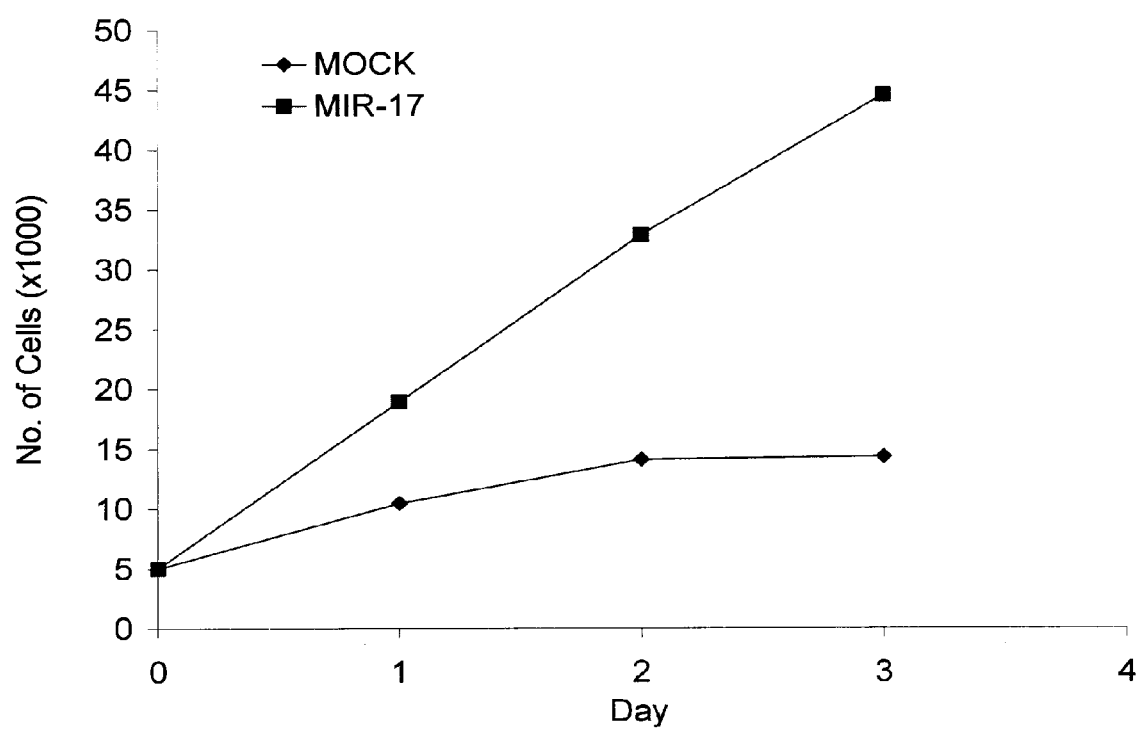
FIG. 9 exhibits proliferation of Mock (diamond) or mir-17 (square)-transfected PAG cells.

Forced expression of miR-17 in PAG cells resulted in substantial facilitation of proliferation (FIG. 9), but not of invasion, tube formation or in vivo tumor growth.

Example 5

Figure 10A:
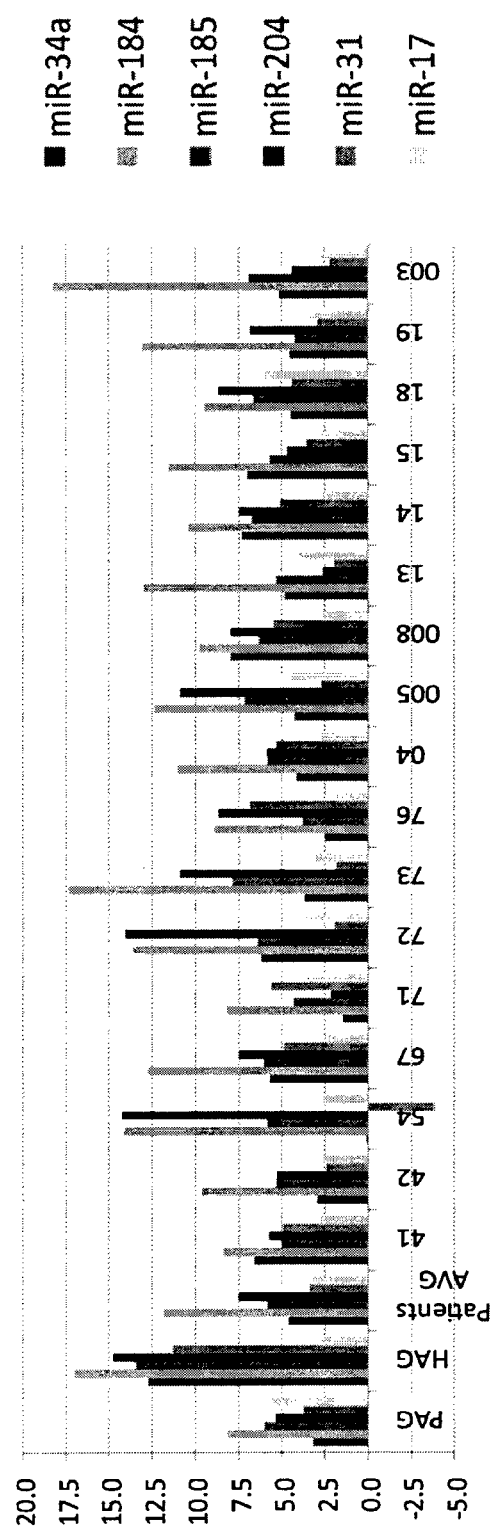
FIG. 10 presents the expression levels, in units of ΔCt (absolute, non-relative, values) of miRs-17, -31, -34a, -133a, -184 and -185 in specimens derived from 15 metastatic melanoma patients (A and B).
Figure 10B:
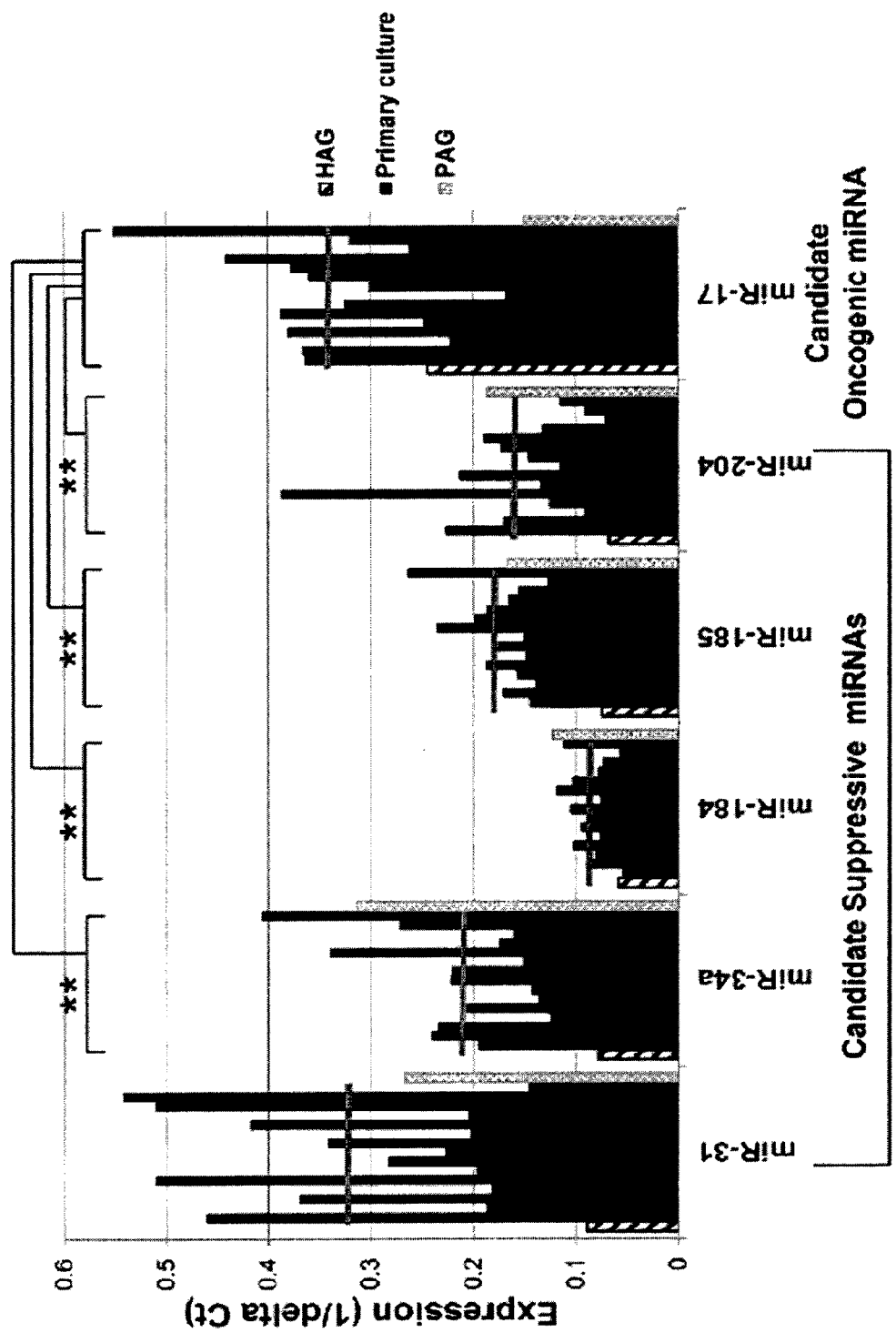

Expression of Exemplar Suppressive and Oncogenic miRs in Specimens of Metastatic Melanoma The expression levels of miRs-17, -31, -34a, -133a, -184 and -185 were determined in specimens derived from 15 metastatic melanoma patients. Expression was normalized in each of the specimens to the U6 endogenous control. All specimens were compared to the poorly aggressive PAG cells (FIG. 10A) or to HAG and PAG cells (FIG. 10B).

All melanoma cultures were established from distant metastases. The analysis established a considerable variability in miRNA expression among the individual specimens (FIG. 10B, black bars), mainly of miR-31 (FIG. 10B). The mean expression level (FIG. 10B, horizontal lines) of most candidate suppressive miRNAs in the clinical specimens was between the corresponding miRNA values in the PAG and HAG cells (FIG. 3B, gray bars and striped bars, respectively), except for miR-185 and miR-31. While the mean level of miRNA-185 was very close to the PAG cells, miRNA-31 levels were clearly higher even than PAG cells (FIG. 10B). In contrast, the mean expression of the candidate oncogenic miR-17 among the clinical specimens was even higher than in HAG cells (FIG. 10B). The miRNA expression patterns in clinical specimens directly shows that most candidate suppressive miRNAs, except for miR-31, are expressed at significantly lower levels than the candidate oncogenic miR-17 (FIG. 10B). These results establish that the approach used to identify functional suppressive and oncogenic miRNAs has physiologically-relevant grounds.

In most cases, the expression of all tested miRs in the melanoma specimens lies within the range between the PAG and the HAG. This observation validates the expression of miRs in clinical melanoma samples. Further, this observation may be used as an inclusion criterion for miR-based therapy (e.g. a patient with a low expression of a certain suppressive miR is expected to benefit from induction of this miR more than would benefit another patient having already high expression of the same suppressive miR).

Example 6

Expression of Circulating miRs and Cluster Analysis

Figures 11A, 11B:
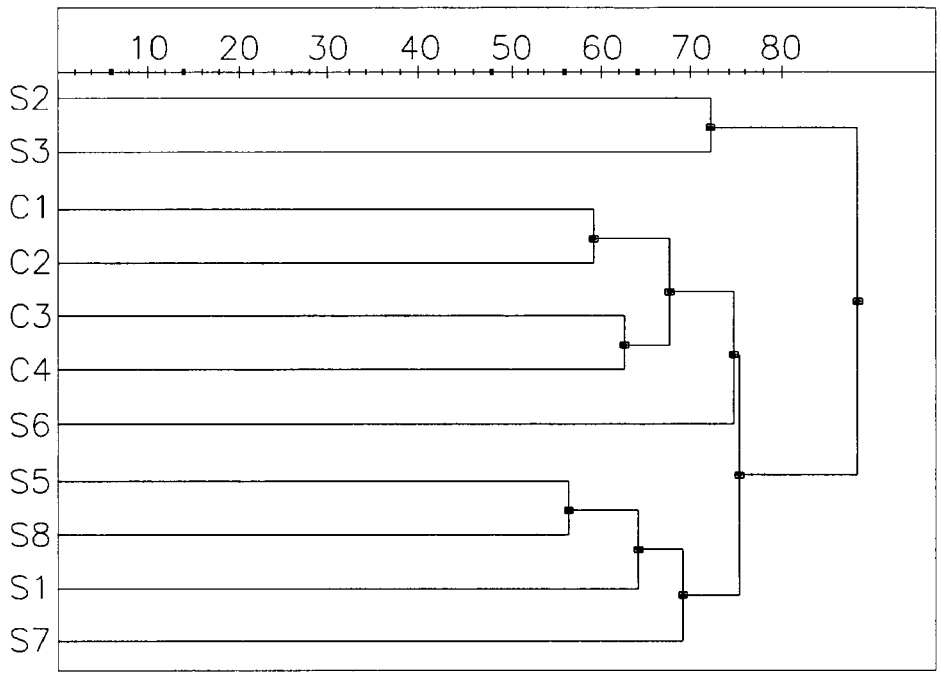
FIG. 11 shows a cluster analysis of subjects according to circulating SNORD-38b, the miR-374 and miR-301 expression profile: (A) shows a dendrogram of control subjects (C1-C4) and melanoma patients (S1-S3, S5-S8); (B) is a list of statistically significant miRs that are different among controls and patients.

A comparative study including 4 healthy controls and 7 melanoma patients was conducted. All subjects were males within the age range of 32-37 y.o., without any detected co-morbidities and were not treated with any chronic medications. Total RNA was extracted from 200 ul of peripheral blood and served as template for generation of cDNA (Exiqon). Circulating miR expression was detected with LNA technology (Exiqon) using qPCR. The complete circulating miR profile was compared between the two groups after normalization using an internal normalizer. As depicted in FIG. 11A, all healthy donors (C1-4) clustered together, while melanoma patients were clustered into two distinct groups: a) S1 and S5-8 (FIG. 11A, Right); b) S2-S3 (FIG. 11A, Left), confirming that distinct characteristics differentiate between the healthy patients and the melanoma patients within the miR expression data. Thirteen miRs exhibited a significantly different expression level between healthy donors and melanoma patients (FIG. 11B).

Example 7

Figure 12:
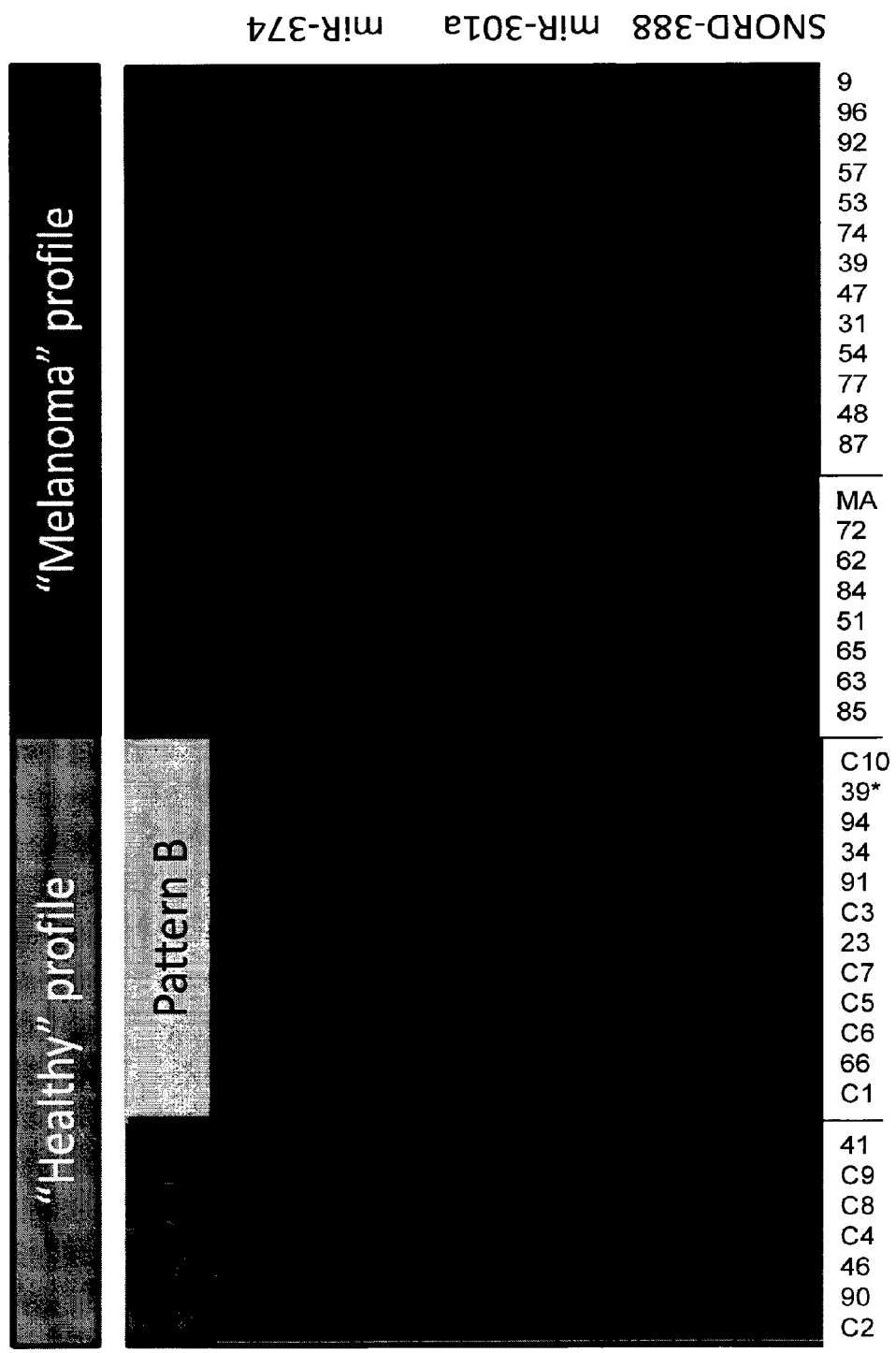
FIG. 12 shows a cluster analysis of subjects according to circulating miR-374, miR-301a and SNORD-38b represented by a Heat map of the indicated miRs in controls (C1-C10), in metastatic melanoma patients (numbers) and in a stage III patient with no evidence of disease (MA). Intense expression is denoted by darksome color, while moderate expression is denoted by light color.

Cluster Analysis of Subjects According to Circulating miR-374, miR-301a and SNORD-38b A comparative expression study including 30 melanoma patients (designated 9, 23, 31, 34, 39, 41, 46-48, 51-54, 57, 62-66, 72, 74, 77, 87, 90, 91, 94 and 96 in FIG. 12) and 10 healthy individuals (control subjects designated C1-C10 in FIG. 12) matched for sex and age was conducted as described above (Example 6). Three miRs displayed high differences that were statistically significant: miR-374, miR-301 and, SNORD-38b, which had a mean difference between the groups of 5 cycles (=64-fold), 2.8 cycles (=7-fold) and 3.9 cycles (=15-fold), respectively. Cluster analysis shows that 21 of the patients (70%) had one of two distinct profiles (FIG. 12). In one profile, an intense expression was detected for the SNORD-38b, the miR-374 and the miR-301. However, in the second profile, while the SNORD-38b and the miR-374 were expressed intensively, the miR-301 was only moderately expressed. None of the healthy donors exhibited any of these two profiles (FIG. 12, light gray). A more complex combination identified 25 of the patients (83.3%), but gave a false positive of one healthy donor.

The results demonstrate that specific fingerprint patterns differentiate groups of interest, such as healthy subjects from melanoma patients, thereby facilitating the reliability of testing circulating miRs.

Example 8

Cluster Analysis of Subjects According to 15 Circulating miRs

Figure 13:
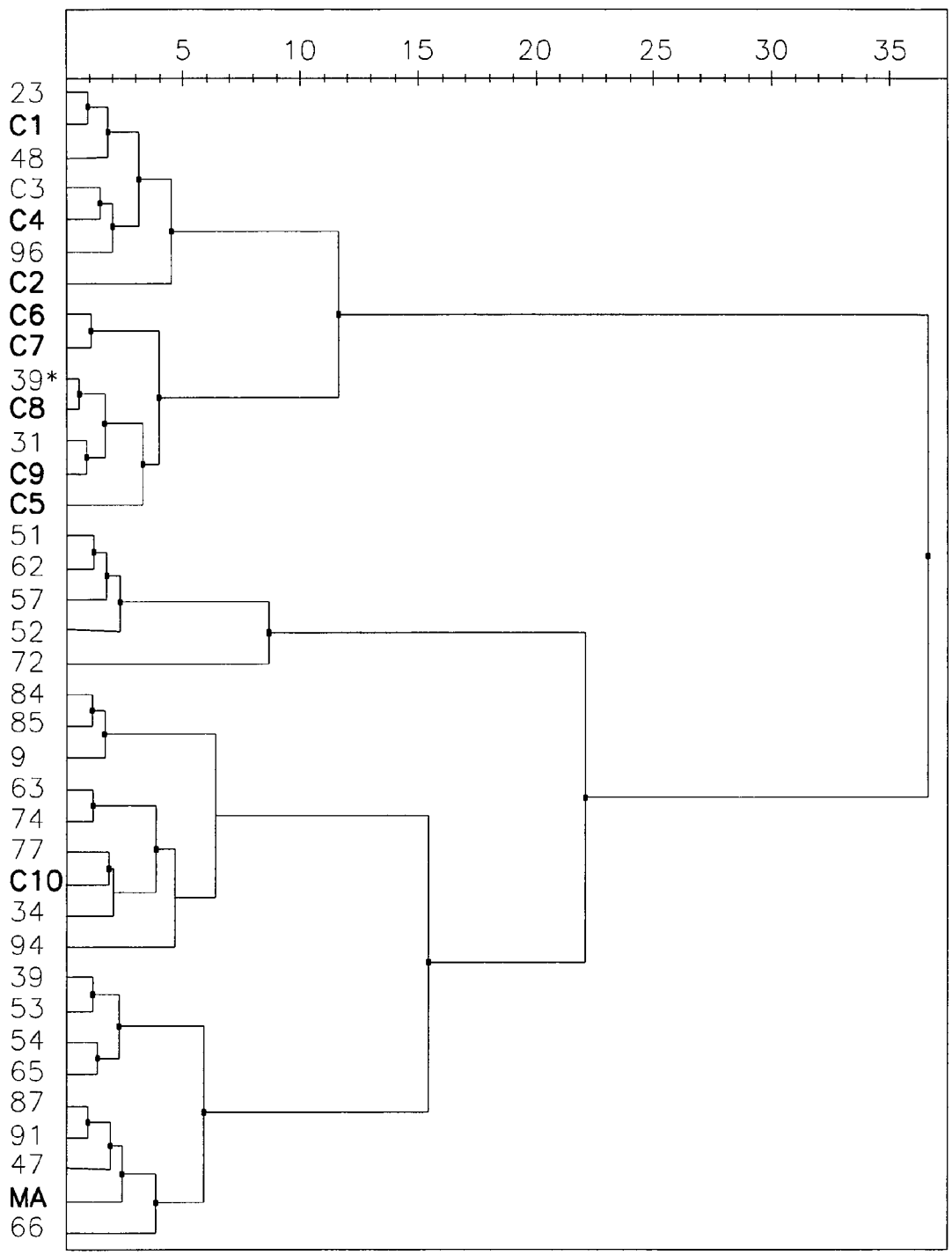
FIG. 13 is a dendrogram of control subjects (C1-C10) and melanoma patients (designated by number) for circulating miR-29c, miR-324-3p, miR-451 and miR-29a and miR-374.

A comparative expression study including 26 melanoma patients (designated 9, 23, 31, 34, 39, 39*, 47-48, 51-54, 57, 62-63, 65-66, 72, 74, 77, 84, 85, 87, 91, 94 and 96 in FIG. 13) and 10 control subjects (designated C1-C10 in FIG. 13). It is noted that patient no. 39 and 39* refer to samples derived from the same patient but at different stages of the disease and therefore, for the purpose of the present analysis, considered as two different samples/patients. The following miRs were analyzed: miR-29, miR-324p, miR-451, SNORD-38b, miR-374a, miR-150, miR-29a, miR-301a, miR-342-3p, miR-339-3p, miR-628-3p, miR-20a*, miR-503, miR-197 and miR-140-3p.

Complete statistical analysis of all subjects with respect to the fifteen miRs is shown in FIG. 14.

Five miRs displayed high differences that were statistically significant: miR-29c, miR-324-3p, miR-451 and miR-29a and miR-374, as shown in Table 3:

TABLE 3

| Analysis of five miRs | |
|---|---|
| miR | T-text (control vs. patient) |
| miR-29c | 0.000157446613038736 |
| miR-324-3p | 0.000518086300203002 |
| miR-451 | 0.01083902330494462 |
| miR-374a | 0.0492456711366369 |
| miR-29a | 0.0576881855462212 |

A dendogram analyzing all subjects with the five significant miRs (miR-29c, miR-324-3p, miR-451, miR-374a and miR-29a) is presented in FIG. 13. As depicted, all control subjects were clustered on the top panel of the dendogram, excluding C10, while most of the patients were clustered in the bottom panel.

Example 9

Retrospective Comparative miR Expression Profile Analysis in Melanoma Tissue Samples of Patients Treated with Ipilimumab Tumor tissues are obtained from patients treated with Ipilimumab, and Laser-Capture-Microdissection (LCM) is employed, thereby dissecting the melanoma tissue from melanoma tissue slides. At least 20 of the samples are derived from patients that experienced clinical benefit from Ipilimumab, and at least 20 are derived from patients that did not respond to the treatment. The miRs are efficiently recovered from paraffin blocks.

Total RNA is purified from the dissected tissue samples and converted into cDNA. The cDNA is analyzed in 10 responders and 10 non-responders by qPCR-based high-throughput miR analysis cards (Applied Biosystems). Expression patterns between the two groups of patients is analyzed with GenEx software and a provisional differential miR signature is selected. The provisional miR signature is further validated with specific qPCR in additional 10 responders and 10 non-responders, thereby yielding a signature of miRs that will differentiate between Ipilimumab-responders from non-responders in a statistically significant manner.

Example 10

Retrospective Comparative miR Expression Profile Analysis in Melanoma Tissue Samples and Serum Samples of Patients Treated with Vemurafenib Tumor tissues are obtained from approximately 50 patients treated with Vemurafenib (around 50% response). The same methodology described in Example 8 is implemented including microdissection, extraction of RNA, high throughput screening on 10 responders and 10 non-responders, analysis of the results and selection of provisional signature. The final step includes validation of the provisional signature with specific qPCR in additional 10 responders and 10 non-responders, thereby yielding a signature of miRs that differentiate between Vemurafenib-responders from non-responders in a statistically significant manner.

Peripheral blood samples are obtained from all patients at time point 0. Total RNA is purified from the serum and cDNA is generated. The entire miR expression profile is tested in 10 responders and 10 non-responders, in order to identify a provisional miR signature in the blood. The provisional signature is validated in additional samples with specific qPCR, thereby yielding an independent signature of response associated miRs, or enhancing the accuracy of the tissue miR signature in predicting response to treatment with Vemurafenib.

Example 11

Regulation of Target Sites by Identified miRs

The identified tissue-miRs from Examples 8 and 9 are analyzed with miR-Path and TargetScan algorithms which predict miRs target sites. In addition, the identified tissue-miRs are cloned into pQCXIP vector which are transduced into a melanoma cell line. The transduced cells are tested for proliferation, invasion through matrigel and in cytotoxicity experiments with reactive antigen-restricted T cells. Further mechanistic investigation is focused on the miRs that exhibit the most promising data, i.e. provide the strongest clinical predictive value and have the strongest effect in vitro.

The transduced cells are tested with whole genome oligonucleotide microarrays and compared to melanoma cells transduced with an empty vector. Crossing of the list of down-regulated genes with the list of potential targets generated by TargetScan narrows the possibilities significantly. The effect on target genes is validated with qPCR. Direct regulation of target sites by the miRs is verified with dual luciferase (Renilla/Firefly) assays. The effect on validated direct targets is determined at the protein level.

Example 12

Prospective-Retrospective Validation of the Predictive miR Signatures

Subjects are not segregated to responders/non-responders, and are blindly tested for the expression of the "relevant" signature only (3-4 response associated miRs identified in Example 9 for Ipilimumab and other 3-4 response associated miRs identified in Example 10 for Vemurafenib). The miR signature in the serum is tested similarly for Vemurafenib only. The ability of the miR signatures to prospectively predict in a blind manner the response to the appropriate treatment is tested prospectively and verified against the clinical outcome retrospectively.

Example 13

Retrospective Comparative miR Expression Profile Analysis in Serum Samples Derived from Patients Treated with Ipilimumab The entire miR expression profile is tested in 10 responders and 10 non-responders, in order to identify a differential provisional miR signature in the blood. The provisional miR signature is further validated in additional samples with specific qPCR, thereby yielding an independent signature of few response associated miRs or enhancing the accuracy of the tissue miR signature in predicting response to treatment with Ipilimumab.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:
1. A method for diagnosing melanoma in a subject, the method comprising:
 (a) obtaining from the subject a sample of peripheral blood comprising RNA; and
 (b) determining, in said RNA, the presence of a plurality of oncogenic miRNAs (miRs), comprising miR-374a and at least one miRNA selected from the group consisting of: miR-301a, SNORD-38b, miR-29c, miR-342-3p, miR-451 and miR-29a,
 wherein the presence of the plurality of oncogenic miRs is indicative of the subject having melanoma.
2. The method of claim 1, wherein the plurality of oncogenic miRs further comprises one or more miRs selected from the group consisting of: miR-150, miR-197, miR-140-3p, miR-503, miR-339-3p, miR-628-3p and miR-20a*.
3. The method of claim 2, comprising determining the presence of miR-374a and at least one miR selected from the group consisting of miR-301a, SNORD-38b, miR-29c, miR-342-3p, miR-451, miR-29a, miR-150, miR-197, miR-140-3p, miR-503, miR-339-3p, miR-628-3p and miR-20a*.
4. The method of claim 2, wherein determining the presence of the plurality of oncogenic miRNAs, comprises:

(a) reverse transcribing the RNA to provide a set of target oligodeoxynucleotides;
(b) hybridizing the target oligodeoxynucleotides to a microarray comprising oncogenic miRNA-specific probe oligonucleotides comprising miR-374a, and at least one oncogenic miRNA-specific probe oligonucleotide selected from the group consisting of miR-301a, SNORD-38b, miR-29c, miR-451, miR-29a, miR-150, miR-342-3p, miR-197, miR-140-3p, miR-503, miR-339-3p, miR-628-3p and miR-20a*, to provide a hybridization profile for the test sample; and
(c) comparing the normalized test sample hybridization profile to a normalized hybridization profile generated from a control sample, wherein significantly different expression of a plurality of oncogenic miRNA relative to the control sample is indicative of the subject having melanoma.

5. The method of claim 4, further comprising amplifying the target oligodeoxynucleotides prior to hybridization with the microarray.

6. The method of claim 1, wherein the melanoma is selected from the group consisting of: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma and soft-tissue melanoma.

7. The method of claim 1, wherein the plurality of oncogenic miRs is selected from the group consisting of miR-374a, SNORD-38b, and miR-301a.

8. The method of claim 1, wherein the plurality of oncogenic miRs comprises SNORD-38b and miR-374a.

9. The method of claim 1, wherein the plurality of oncogenic miRs comprises miR-374a and at least one miRNA selected from the group consisting of: miR-29c, miR-342-3p, miR-451 and miR-29a.

10. The method of claim 1, wherein the plurality of oncogenic miRs comprises at least three oncogenic miRs.

11. The method of claim 10, wherein the plurality of oncogenic miRs comprises at least four oncogenic miRs.

* * * * *